(12) United States Patent
Hardahl et al.

(10) Patent No.: US 8,260,406 B2
(45) Date of Patent: Sep. 4, 2012

(54) SYSTEM AND METHOD FOR ANALYZING COMPLEX CURVATURE OF ECG CURVES

(75) Inventors: Thomas Bork Hardahl, Aalborg (DK); Claus Graff, Klarup (DK); Mads Peter Andersen, Aalborg OEst (DK); Egon Toft, Aalborg OE (DK); Johannes Jan Struijk, Aalborg OEst (DK); Joel Q. Xue, Wauwatosa, WI (US)

(73) Assignee: Aalborg Universitet, Aalborg Ø (DK)

( * ) Notice: Subject to any disclaimer, the term of this patent is extended or adjusted under 35 U.S.C. 154(b) by 259 days.

(21) Appl. No.: 12/517,120

(22) PCT Filed: Nov. 28, 2007

(86) PCT No.: PCT/DK2007/000522
§ 371 (c)(1),
(2), (4) Date: Sep. 21, 2009

(87) PCT Pub. No.: WO2008/064679
PCT Pub. Date: Jun. 5, 2008

(65) Prior Publication Data
US 2010/0069767 A1   Mar. 18, 2010

(30) Foreign Application Priority Data
Nov. 30, 2006   (DK) .................................. 2006 01580

(51) Int. Cl.
*A61B 5/04* (2006.01)
(52) U.S. Cl. ..................................................... 600/509
(58) Field of Classification Search ........... 600/509–521
See application file for complete search history.

(56) References Cited

U.S. PATENT DOCUMENTS
6,684,100 B1 * 1/2004 Sweeney et al. ............... 600/517
(Continued)

FOREIGN PATENT DOCUMENTS
WO   2005/002669 A2   1/2005
(Continued)

OTHER PUBLICATIONS
Wojciech Zareba, Genotype-Specific ECG Patterns in Long QT Syndrome, Journal of Electrocardiology, vol. 39, No. 4, Oct. 2006, pp. S101-S106, Abstract.

*Primary Examiner* — Carl H Layno
*Assistant Examiner* — Roland Dinga
(74) *Attorney, Agent, or Firm* — Roberts Mlotkowski Safran & Cole, P.C.; David S. Safran

(57) ABSTRACT

A system and a method for analysis of ECG curvature, which system involves a mathematical analysis comprising the following features where a number of different parameters are isolated and stored in a computer, where a first number of parameters are selected from at least one main group, where the selected parameters are combined in at least a first mathematical analysis. It is the object of the invention to improve mathematical analysis of ECG curvature particular for complex parts of the curvature such as notches or concavities. This can be achieved by selecting parameters from groups of symmetry, flatness, duration and/or complexity, using the parameters as input to an algorithm, where concavity intervals are evaluated on subsegments of the ECG segment and form the basis of up and downwards concavity quantification, where the system based on an algorithm detects and quantifies concavity on ECG curvatures.

19 Claims, 20 Drawing Sheets

Flow diagram of algorithm

U.S. PATENT DOCUMENTS

| | | | |
|---|---|---|---|
| 7,072,708 B1 * | 7/2006 | Andresen et al. | 600/509 |
| 2004/0010200 A1 * | 1/2004 | Sweeney | 600/517 |
| 2004/0267143 A1 * | 12/2004 | Sweeney | 600/509 |
| 2005/0177049 A1 * | 8/2005 | Hardahl et al. | 600/509 |
| 2005/0234357 A1 | 10/2005 | Xue et al. | |
| 2007/0203419 A1 * | 8/2007 | Sweeney et al. | 600/510 |

FOREIGN PATENT DOCUMENTS

| | | | |
|---|---|---|---|
| WO | 2005/058156 A1 | 6/2005 | |
| WO | WO 2005/058156 * | 6/2005 | 600/509 |

* cited by examiner

Flow diagram of algorithm

Normalized ECG segment from J-point+80ms to the following Pwave onset. Fiducial points Twave onset, Twave peak and Twave offset are indicated by vertical dashed lines.

Local maxima (LmRcurv) on the radius of curvature signal (Rcurv) indicated by red + marks. Values inside the Twave peak window on the Rcurv are set to equal one and are not used for further analysis.

Fig. 4    Downwards concavity certainty measures (Cm) indicated by red stems

All combinations of intervals between local maxima on the second derivative signal shown as 6 horizontal solid lines.

Tilted subsegments T$_{1tilt}$ and T$_{2tilt}$.

Final maximum downwards concavity interval. Downwards concavity score (CdS) is given by the maximum difference between the angled line and the Twave Fig. 8  Concavity scores for the electrocardiographic lead V5

SYSTEM AND METHOD FOR ANALYZING COMPLEX CURVATURE OF ECG CURVES

FIELD OF THE INVENTION

The present invention relates to a system and a method for analysis of ECG curvature, which system involves a mathematical analysis, which mathematical analysis comprises at least the following features a number of different parameters are isolated and stored in a computer system, where the system comprises input means connected to at least one ECG source, where a first number of parameters are selected from at least one main group, which main groups comprise parameters of symmetry, flatness, duration and/or complexity, where the selected parameters are combined in at least a first mathematical analysis.

BACKGROUND OF THE INVENTION

An article describes Notched T Waves on Holter Recordings Enhance Detection of Patients With LQT2 (HERG) Mutations J. M. Lupoglazoff, MD; I. Denjoy, MD; M. Berthet; N. Neyroud, PhD; L. Demay; P. Richard, PhD; B. Hainque, PhD; G. Vaksmann, MD; D. Klug, MD; A. Leenhardt, MD; G. Maillard, MD; P. Coumel, MD; P. Guicheney, PhD The 2 genes KCNQ1 (LQT1) and HERG (LQT2), encoding cardiac potassium channels, are the most common cause of the dominant long-QT syndrome (LQTS). In addition to QT-interval prolongation, notched T waves have been proposed as a phenotypic marker of LQTS patients. The T-wave morphology of carriers of mutations in KCNQ1 (n5133) or HERG (n557) and of 100 control subjects was analysed from Holter ECG recordings. Averaged T-wave templates were obtained at different cycle lengths, and potential notched T waves were classified as grade 1 (G1) in case of a bulge at or below the horizontal, whatever the amplitude, and as grade 2 (G2) in case of a protuberance above the horizontal. The highest grade obtained from a template defined the notch category of the subject. T-wave morphology was normal in the majority of LQT1 and control subjects compared with LQT2 (92%, 96%, and 19%, respectively, P, 0.001). G1 notches were relatively more frequent in LQT2 (18% versus 8% [LQT1] and 4% [control], P, 0.01), and G2 notches were seen exclusively in LQT2 (63%). Predictors for G2 were young age, missense mutations, and core domain mutations in HERG. This study provides novel evidence that Holter recording analysis is superior to the 12-lead ECG in detecting G1 and G2 T-wave notches. These repolarization abnormalities are more indicative of LQT2 versus LQT1, with G2 notches being most specific and often reflecting HERG core domain missense mutations. (Circulation. 2001; 103:1095-1101.)

Further is described Quantitative Analysis of T Wave Abnormalities and Their Prognostic Implications in the Idiopathic Long QT Syndrome GABRIELLA MALFATTO, MD,*t GABRIELLA BERIA, MD,*$ SERGIO SALA, MD,*t OSCAR BONAZZI, MD,* PETER J. SCHWARTZ, MD, FACC*§ Milan and Pavia, Italy.

We evaluated the diagnostic and prognostic value of morphologic abnormalities of the T wave (mainly notched or biphasic T waves) in patients affected by the idiopathic long QT syndrome. In the long QT syndrome, these abnormalities in T wave morphology are often observed and are of uncertain significance. The T wave abnormalities in the electrocardiogram (ECG) of 53 patients with the long QT syndrome and 53 control subjects of similar age and gender were analyzed, and their association with major cardiac events was defined. Notched or biphasic T waves were defined according to morphologic criteria. They were present in 33 (62%) of 53 patients with the long QT syndrome and in 8 (15%) of 53 control subjects ($p<0.001$). Moreover, among patients with the long QT syndrome they were much more frequent in symptomatic (history of syncope or cardiac arrest) than in asymptomatic subjects (30 [81%] of 37 vs. 3[19%] of 16, $p<0.001$). The same distribution was observed within families with the long QT syndrome, in which symptomatic members had more pronounced T wave abnormalities than did their asymptomatic siblings or parents. In symptomatic patients, the occurrence of T wave abnormalities was independent of the length of repolarization (corrected QT). These 'I wave abnormalities were associated with the presence of a specific pattern of abnormal left ventricular wall motion. This study has quantified an ECG pattern typical of the long QT syndrome and provides the first evidence that morphologic analysis of T wave abnormalities may contribute to the diagnosis of the long QT syndrome and the identification on patients at higher risk for syncope or cardiac arrest.

Further, an article entitled "T-wave "Humps" as a Potential Electrocardiographic Marker on the Long QT Syndrome" by MICHAEL H. LEHMANN, MD, FACC, FU-MIO SUZUKI, MD, BARBARA S. FROMM, MA, DEBRA FRANKOVICH, RN, PAUL ELKO, PhD, * RUSSEL T. STEINMAN, MD, FACC, JULIE FRESARD, RN, † JOHN J. BAGA, MD, R. THOMAS TAGGART PhD* is described.

This article describes a study attempted to determine the prevalence and electrocardiographic ECG lead distribution on T wave humps (T2 after an initial T wave peak, T1) among families with long QT syndrome and control subjects. T wave abnormalities have been suggested as another facet of familial long QT syndrome in addition to prolongation of the rate corrected QT interval (QTc) that might aid in the diagnosis of affected subjects. The ECG from 254 members of thirteen families with long QT syndrome (each with two or four generations of affected members) and from 2948 healthy control subjects ($8\geqq16$ years QTC intervals of 0.39 to 0.46 s) were collected and analysed. T2 was present in 53%, 27% and 5% of blood relatives with a prolonged QCT interval. These findings are consistent with hypothesis that in families with long QT syndrome, T wave humps involving left precordial or especially limps leads, even among asymptotic blood relatives with borderline QCT interval, suggested the presence of the long QT syndrome trait.

An article concerns Fractionated Repolarization Induced by Sotalol in Healthy Subjects M Vaglio, J P Couderc, X Xia, W Zareba Heart Research Follow-up-Program University of Rochester Medical Center, Rochester N.Y., USA.

Over the past five years, regulatory authorities have been increasingly concerned with QT prolongations induced by non-cardiac drug and have recommended pharmaceutical companies to include a careful assessment of the QT interval in their drug development programs. There are controversies around the predictive value of QT prolongation in safety-drug assessment studies. The prolongation of the QT interval is an imperfect, but accepted, surrogate marker of drug cardiac toxicity. In this study, we hypothesize that the inhomogeneous effect of QT prolonging drug in the different layers of the myocardium would not only delay cardiac repolarization, but also perturb the repolarization wavefront on surface ECGs. Principal component analysis (PCA) was applied to the L2-lead ECG Holter recordings. The first two eigenvectors (eu1, eu) were computed. From PCA, several parameters were calculated based on the first eigerwector and on the T-loop. We demonstrated slower repolarization and perturbed T-wave front; 30 min after sotalol administration, turbulence of repolarization velocity increased by 9.02%, p<0.05, occurring prior to QT prolongation. These abnormalities were mainly located in the ascending part of the T-wave, where as the descending part seemed to be less affected at this early phase. In conclusion, analyzing repolarization morphology might help identifying early drug-induced repolarization changes, which could be missed when relying exclusively on QT measurements.

The four mentioned articles all concern manual detection of ECG curvatures. Hundreds of curves have to be analysed manually in order to read the results mentioned in these articles. The manual method is effective for determination for a single patient, but only highly educated medical specialists are able to analyse the curvature. When such a judgement of ECG curvatures is only for specialists, they have to spend several hours per day just to analyse ECG curvatures. An open question is how effective even highly trained specialists are after having analysed curvatures for hours. There is always the risk that they overlook small deviations in the curvature. Due to a computerised curvature, analysis is much more effective, and a much higher number of curvatures can be analysed in a rather short period. There is not any risk that the computer system will overlook deviations in the curvature. A computerised system can make an effective selection between patients with deviations in the curvature and healthy people with a normal curvature.

EP 1 543 770 concerns a system or a method for analysing ECG curvature where at least one among a number of different parameters is isolated, which system has an input means connected to an ECG source, where the different parameters of a received ECG curvature are indicated and/or isolated and for indicating possible symptoms which relate to or are indications of certain deceases, where said deceases are known to influence the ECG curvature. First number of selected parameters are combined in at least a first mathematical analysis, where the result of the analysis can be represented as a point in a coordinate system comprising at least two axes where the system can compare the actual placement in the coordinate system with a number of reference parameters stored in the system for indicating diseases having influence on the ECG curvature. Hereby, it is achieved that any symptom of a disease having an indication (influence) in the ECG curvature can be detected in an objective and automated way.

WO 2005/058156 concerns a system or a method for analysing drug influence on ECG curvature and Long QT Syndrome where at least one among a number of different parameters is isolated, which system has a input means connected to an ECG source, where the different parameters of a received ECG curvature are indicated and/or isolated and for indicating possible symptoms which relates to or are indications of certain diseases, where said diseases are known to influence the ECG curvature. The aim of the invention is to achieve a system and a method for diagnosing Long QT Syndrome in an objective, fast and effective way by indication of a number of symptoms derivable from an ECG curve. Further aim of the invention is to achieve an effective test of drug influence on ECG curvature. This can be achieved with the system previously described if a first number of selected parameters is combined in at least a first mathematical analysis, where the result of the analysis can be represented as a point in a coordinate system comprising at least one axis where the system can compare the actual placement in the coordinate system with a number of reference parameters stored in the system for indicating symptoms or diseases having influence on the ECG curvature, where the system analyses the QT curvature of the ECG curvature for indicating Long QT syndrome. Hereby, it is achieved that any symptom of hereditary or acquired Long QT Syndrome having an indication (influence) in the ECG curvature can be detected in an objective, automated and very fast way.

US 2005/0234357 concern a method and apparatus for detecting cardiac repolarization abnormality using at least one electrocardiogram signal. The at least one electrocardiogram signal can be obtained from any number of continuous or non-continuous windows. The method can include deriving a total quantity of representative beats of the at least one electrocardiogram signal. At least one morphology shape descriptor can be used to determine a total quantity of values representing the total quantity of representative beats. Data corresponding to at least some of the total quantity of values can be used to assess cardiac repolarization abnormality.

U.S. Pat. No. 7,072,708 concerns a method in a computer system for detecting myocardial infarction including the steps of (a) receiving ECG data, (b) analyzing that data for the presence of benign ST data, and (c), when the ST data is not benign, (1) establishing a pathological threshold, (2) normalizing any deviation in the ECG data, (3) applying a pattern analysis to the normalized ECG data, and (4) generating a score indicating the presence of a myocardial infarction based on the pattern analysis and the threshold.

WO 2005/00269 concern implantable cardiac rhythm management device e.g. pacemaker, determines fundamental frequency of sampled signal by autocorrelating function of series of characteristic points each having time of lobe in curvature series. This can be achieved by estimating a frequency of a sampled cardiac rhythm signal and classifying the rhythm. The received signal is sampled and transformed into a curvature series. A lobe in the curvature series corresponds to a characteristic point in the sampled series. Characteristic points are selected based on a time of a lobe in the curvature series and, in one embodiment, amplitude of the signal at the time of the lobe. A frequency of the sampled series is estimated by autocorrelating a function of the series of the characteristic points. In one embodiment, the function is a time difference function. The rhythm is classified by plotting the timewise proximity of characteristic points derived from an atrial signal with characteristic points derived from a ventricular signal. Regions of the plot are associated with a particular rhythm and the grouping of the data corresponds to the classification.

OBJECT OF THE INVENTION

It is the object of the invention to improve mathematical analysis of ECG curvature particular for complex parts of the curvature such as notches or concavities.

It is a further object of the invention to improve automatic quantification of symmetry, flatness and durations of ECG curvature.

DESCRIPTION OF THE INVENTION

This can be achieved in a system as described in the preamble to claim 1 and further modified so that the parameters are selected from groups of symmetry (S1-S72), flatness (F1-91), duration (D1-D47) and/or complexity (C1-C468), where the mathematical analysis involves the action of extracting a segment of the ECG curvature, which segment is corresponding to the interval between defined electrocardiographic points, which segment is used as input to a first algorithm, where a second fiducial point algorithm automatically calculates fiducial points at the segment, where concavity intervals are evaluated on subsegments of the ECG segment and form the basis of up- and downwards concavity quantification, where the system based on the first and the second algorithm detects and quantifies concavity on ECG curvatures.

Herby can be achieved that a complex curvature can be analysed and the complex curvature might indicate symptoms of diseases which are very difficult to read on ECG curvature by existing technology. This can lead to a more precise analysis where existing systems might by analysing the curvature give a first indication of a symptom. By then performing an analysis of the complex part of the curvature, further symptoms might be indicated. This could lead in the direction of a more precise judgement of a disease. This can by computerised analysis of ECG curvature lead to a very limited overlap between curvatures judged as belonging to healthy persons and curvatures judged as belonging to persons carrying a disease. In normal computerised analysing, these overlaps might concern a relative great number of persons who have been analysed. Here, it is necessary to perform manual analysis of the ECG curvature and probably further medical analysis in order to make a clear decision of who carries a disease and who carries health. In the future, there will probably be developed further diseases specific symptoms based on complex deviations on ECG curvature.

At least one segment of the ECG repolarization signal can be selected, corresponding to the interval between the T wave onset and T wave offset, which segment is normalized so that the amplitude range (y) is equal to one in the selected interval. Hereby is achieved that on a selected part of the curvature between the T wave onset and the Twave offset is normalised show over the selected part of the curve the mean value of this curve will be a straight line. Deviations are the easy to read simply because they represent deviations from the straight line. It is to be understood that by a very primitive amplification of the signals these deviations on the straight line are very easy to amplify to a rather high value where even small deviations are easy to detect.

At least one segment of the ECG repolarization signal is selected, corresponding to the interval between the T wave onset and T wave offset, which segment is normalized so that the duration (x) is equal to one in the selected interval. Hereby is achieved that the duration is normalised. This can lead to a rather high amplification of the duration such that it is very easy to indicate any deviations where even small deviations will be amplified and in this way it is able to measure even very small deviations in the time domain.

The first and second derivatives with respect to time of the ECG repolarization segment are determined on the interval between the Twave onset and Twave offset, where the two derivative signals are subsequently used to calculate a radius of curvature (Rcurv) signal using the equation 1:

$$Rcurv = -\frac{\left[1 + \left(\frac{dy}{dx}\right)^2\right]^{3/2}}{\frac{d^2y}{dx^2}} \quad \text{Equation 1}$$

where x is the timescale and y is the (ECG) signal. Hereby is achieved that a calculation of the radius of a curvature is achieved.

Local maxima (LmRcurv) on the Rcurv signal between any two repolarization fiducial points is determined to identify places of local downwards concavity on a repolarization segment of an ECG. Hereby is achieved that the points of local maximum is identified in a highly effective way.

Local minima on the Rcurv signal between any two repolarization fiducial points are determined to identify places of local upwards concavity on a repolarization segment of an ECG. Hereby is achieved that the point of local minima is identified in a highly effective way.

The peak of the Twave (Tpeak) typically constitutes a local maximum of the Rcurv signal. The Rcurv signal can be analyzed further to investigate if further maxima and minima exist. If a contiguous configuration of local maximum neighbored by local minimum exists on the Rcurv signal, this may be indicative of a notch or hump on the ECG signal. The value of the Rcurv signal in the relevant maximum and minimum may be evaluated to quantify the size of the notch or hump on the ECG signal. Hereby is achieved a simple and robust method for identifying and quantifying notches and humps on the ECG signal.

A window can be defined in a curve segment starting at a first defined period before T wave peak and ending at a second defined period after T wave peak, in which window the curvature is excluded from further analysis of the Rcurv signal, and where any number of LmRcurv signal values with amplitudes below zero is excluded from further analysis, where any number of LmRcurv signal values, which correspond in time to ECG repolarization amplitudes below any given threshold are excluded from further analysis. Hereby is achieved that certain areas of a curvature are blanked out from the analysis. These areas are probably that part of the curvature which contains the most noise, and which contains relative new information in that part of the curvature.

Positive segment durations on the Rcurv on either side of all reference points are multiplied by the value of the corresponding LmRcurv values to obtain certainty measures (Cm) of the presence of local downward concavities. Hereby, it is achieved that the downward concavities are multiplied by a factor such that they become visible also for the further analysis of the curvature.

Certainty measures exceeding a threshold (Thr) are defined as places around which concavity intervals are defined and local downward concavities are quantified. By using a threshold value, it can be achieved that very small downward concavities are blanked out of the analysis. This might be done simply because some of very small downward concavities are results from noise which has been generated may be in the human body of may be electrical noise induced in the system.

No certainty measures exceeding a threshold (Thr) are present, where a first subsegment is generated by two piecewise tilted segments, where a first tilted subsegment ($T_{1tilt}$) is given by the repolarization interval between the T wave onset and T wave peak from which the linear function between the two endpoints is subtracted, where a second tilted subsegment ($T_{2tilt}$) is given by the repolarization interval between the T wave peak and T wave offset from which the linear function between the two endpoints is subtracted.

An upwards concavity score is calculated, where the least negative maximum on either piecewise repolarization subsegment is used as an initial upwards concavity score (IuS), which score is corrected to obtain a final upwards concavity score (CuS) of zero when any certainty measure equals the certainty threshold and a final CuS score equal to IuS when no LmRcurv points remain after the exclusion criteria step, where the relationship is given by equation 3.

$$CuS = IuS\left(1 - \frac{Cm}{Thr}\right). \quad \text{Equation 3}$$

Hereby is achieved that upward concavity is measured.

A subsegment can be generated by two piecewise tilted segments, where a first tilted subsegment is given by the repolarization interval between the T wave onset and T wave peak from which the linear function between the two endpoints is subtracted, where a second tilted subsegment is given by the repolarization interval between the T wave peak and T wave offset from which the linear function between the two endpoints is subtracted. By subtracting the linear relation between the starting point and the top point, all deviations from the linear relation in the up going and the down going curve will be amplified in a way where they are very easy to detect.

On both of the tilted subsegments and all concavity intervals are evaluated and maximum values ($T_{1tiltmax}$) and ($T_{2tiltmax}$) on the tilted subsegments in the concavity intervals are determined, where the overall maximum value is the final concave down score (CdS) of the ECG repolarization segment given by equation 2:

$$CdS = \max([T_{1tilt\,max} T_{2tilt\,max}]).$$   Equation 2

Hereby is achieved that a highly effective measurement of concavity is achieved, which is more indicative of disease or drug influence than manual inspection of ECG curvature.

The peakedness of the T wave peak (Peak_Curvature) is evaluated by calculating the radius of curvature value (Rcurv) in T peak, which radius of curvature is given by:

$$Rcurv = -\frac{\left[1+\left(\frac{dy}{dx}\right)^2\right]^{3/2}}{\frac{d^2y}{dx^2}}$$

where x is the timescale normalized with the T wave width, and y is the ECG signal normalized with the T wave amplitude. Hereby is achieved that the curvature of the peak of the T wave is calculated in an effective way.

The symmetric properties of the T wave are evaluated by comparing the T wave curve on the right side of T peak with the T wave curve on the left side of T peak, which comparison of left and right side is performed at any representation of the T wave, such as the time domain ECG signal, the first derivative of the signal, the second derivative of the signal or any combination of these such as the radius of curvature of the signal Rcurv. Hereby, a highly effective measurement for symmetry is achieved.

The T wave representation of the right side of T peak is flipped around a vertical line through T peak to cover the left side of T peak. In this way, a very easy mathematical calculation can be performed for measuring the symmetry.

A first or second derivative is used for the mathematical analysis, where the T wave representation of the right side of T peak is flipped around the x axis to compensate for the sign difference between the two sides. Hereby, is achieved a highly effective mathematical analysis.

Preferably the system can analyse ECG curvature for drug influence. Drug has often influence on the ECG curvature. For analysing drug, it could be very effective to use an analysis also on the complex part of the ECG curvature in order to indicate negative symptoms by testing new forms for drug.

The system can analyse an ECG curvature for Long QT Syndrome. A system as described in this patent application can very effectively investigate a high number of test persons for long QT syndrome. Especially an analysis using this system will be highly effective because together with a change in the QT also complex changes in the curvature might occur.

The invention further concerns a method for analyse of ECG curvature, which method determines a number of parameters, where the method for analysing the ECG curvature at least incorporates the steps of receiving at least one ECG curvature from at least one source, indicating a number of different parameters determined from the received ECG curvature, storing the parameters in storage means, selecting disease specific parameters in the storage means, selecting a first number of parameters from at least one main group, which main groups comprise parameters of symmetry, flatness, duration and/or complexity, combining the selected parameters in at least a first mathematical analysis, where the mathematical analysis is extracting a segment of the ECG curvature, which segment is corresponding to the interval between defined electrocardiographic points, which mathematical analysis uses the segment as input to an first algorithm to calculate fiducial points at the segment, by a second fiducial point algorithm, which mathematical analysis normalizes the segment of the ECG curvature corresponding to the interval between defined electrocardiographic points in relation to at least one selected parameter, which mathematical analysis evaluates concavity intervals on subsegments of the ECG segment and form the basis of upwards and downwards concavity quantification, which mathematical analysis indicates symptoms of electrocardiographic abnormalities by detection and quantification of at least one concavity of an ECG curvature.

This method could lead to a very effective automatic analysis of ECG curvature. After the analysis of an ECG curvature, the system can communicate with a database containing equal ECG results where a new test of a curvature can be compared with a high number of previous tests of curvatures. In this way, symptoms of the curvature can easily be detected for a patient and related to a specific disease. Also in the drug test, this method can be highly effective. Some kinds of drugs might have an influence on the ECG curvature, but this influence consists only of very small deviations in the curvature. These very small deviations are not being measured in the previous known systems. By using this method, an analysis of a complex part of the curvature is possible.

DETAILED DESCRIPTION OF THE INVENTION 1.1 Parameters for Quantifying Morphology of ECG Curvatures The Long QT Syndrome is a genetic disorder characterized by abnormal cardiac repolarisation. In congenital LQTS, mutations in the KvLQT1- and HERG genes accounts for more than 90% of all LQTS patients.

The abnormality in the repolarisation is reflected in the ECG curves, where the morphology of the T-wave changes regarding to different LQT mutations.

Studies have shown that T-wave morphology parameters are useful discriminators, but no single parameter has shown to be sufficient. However multivariate discrimination method based on combination of T-wave symmetry-, flatness, duration- and complexity parameters, has shown to be a powerful tool.

Various drugs give rise to an influence on the ECG curves, and often similar T-wave morphology changes as seen to LQT patients with mutation in the HERG genes. For that reason quantifying of the morphology changes, in pre-market drug testing would give valuable information in making the decision, whether is should get on the market or not.

Morphology parameters in the groups, symmetry, flatness, duration and complexity gives valuable information about these morphology changes, both as single parameters but especially combined in a multivariate discrimination method.

Patients with mutation in the HERG genes, often have a more convex pattern on the up- and/or down-slope of the T-wave than healthy subjects. Sometimes HERG patients ECG shows a distinct notch on the up- or down-slope of the T-wave.

The group of parameter called complexity comprises i.a. of parameters which measures these complex patterns in the curvature.

By that we mean a measure that describes the concavity versus convexity of respectively the up- and down slope. This is like an overall measure of the up- or down-slopes curve pattern.

Besides that the complexity is also bumpiness/notchness or a distinct notch, which is just a more local concavity or convexity on the curve pattern.

In the following a mathematical description is given of the parameter, which measure these convexity and concavity, whether it's overall or local.

Figure 1:
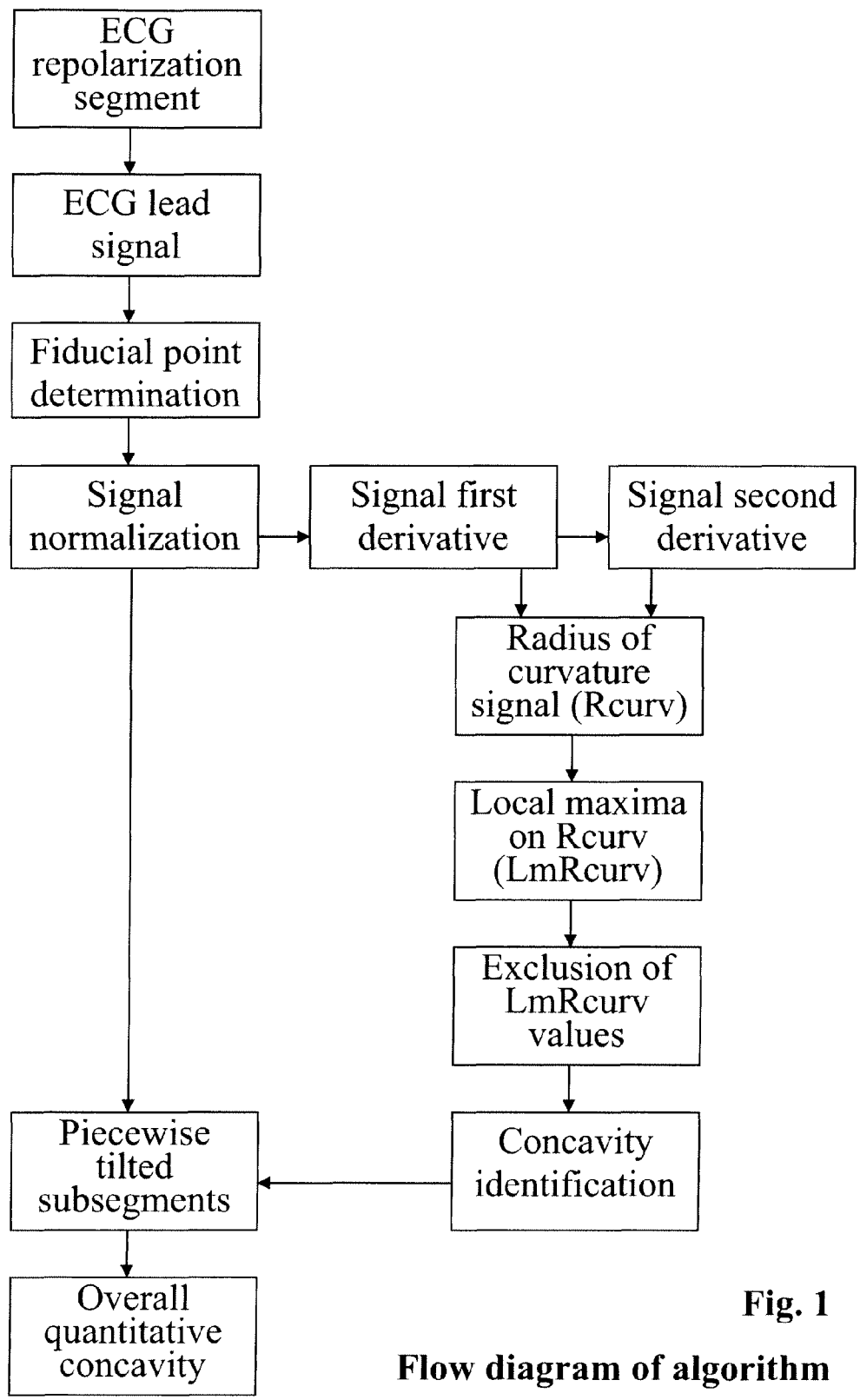
FIG. 1. Flow diagram of algorithm.

1.2 FIG. 1 Shows a Flow Diagram of a Algorithm for Detection and Quantification of Repolarization Concavity on the ECG During repolarization an ECG curvature may be concave up or concave down or it may change between the two forms of concavities. An algorithm has been developed to detect and quantify these two forms of concavity on an ECG during repolarization.

An ECG segment of the repolarization process including as a minimum, the entire electrocardiographic T wave from any one electrocardiographic lead or any composite lead can be used as input to the algorithm. Also, the definitions of repolarization fiducial points such as T wave onset, T wave peak, T wave offset and other repolarization fiducial points can be given by any existing fiducial point detection algorithm, or repolarization fiducial points may be determined by manually.

The algorithm may normalize an ECG repolarization segment in such a way that the amplitude range (y) between any two fiducial points is equal to one. The algorithm may further normalize the duration of the ECG repolarization segment in such a way that the duration (x) between any two repolarization fiducial points is equal to one.

The first and second derivatives of the ECG repolarization segment can be determined and both derivative measures may be used to calculate a radius of curvature (Rcurv) signal between any two repolarization fiducial points. The Rcurv signal can be obtained as follows:

$$Rcurv = -\frac{\left[1 + \left(\frac{dy}{dx}\right)^2\right]^{3/2}}{\frac{d^2y}{dx^2}} \qquad \text{Equation 1}$$

Local maxima (LmRcurv) on the Rcurv signal between any two repolarization fiducial points can be determined. Any number of local maxima in a window of varying duration around a given definition of Twave peak may be excluded from further analysis of the Rcurv signal. Any number of LmRcurv signal values with amplitudes below zero may be excluded from further analysis. Any number of LmRcurv signal values, which correspond in time to ECG repolarization amplitudes below any given threshold may be excluded from further analysis.

All LmRcurv values that have not been excluded from further analysis can be used to identify places of local downwards concavity on a repolarization segment of an ECG. Identified places of local downwards concavity subsequently can form the basis for quantification of local downwards concavity on a repolarization segment of an ECG.

The extent of downwards concavity on an ECG repolarization segment can be evaluated at identified places of local downwards concavity or in intervals around places of identified local downwards concavity.

Piecewise tilted subsegments of a longer ECG repolarization segment may be used to obtain measures of local downward concavities. Piecewise tilted subsegments of a longer ECG repolarization segment may also be used to obtain measures of local upward concavities. The extent of all local downward concavities and local upward concavities on an ECG repolarization segment can be used to obtain a final overall quantitative measure of concavity for that ECG repolarization segment.

A flow diagram of the algorithm is provided in FIG. 1.

1.3 Application Example: Detection and Quantification of Repolarization Concavity on the ECG An ECG segment of the repolarization process corresponding to the interval between the electrocardiographic J-point+ 80 ms and the following electrocardiographic Pwave onset is extracted and used as input to the algorithm.

The Twave onset, Twave peak and Twave offset fiducial points are determined automatically by an existing fiducial point detection algorithm.

Figure 2:
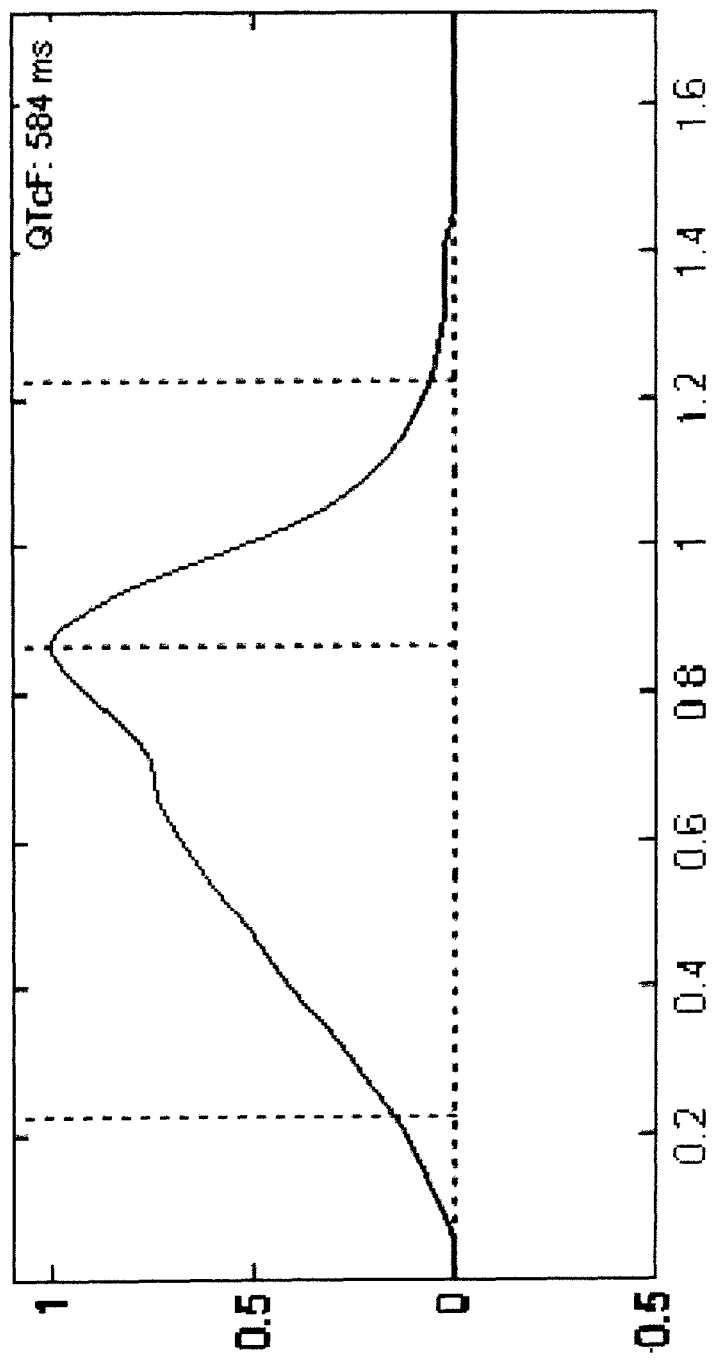
FIG. 2. Normalized ECG segment from J-point+80 ms to the following Pwave onset. Fiducial points Twave onset, Twave peak and Twave offset are indicated by vertical dashed lines.

A segment of the ECG repolarization signal corresponding to the interval between the Twave onset and Twave offset is normalized so that the amplitude range (y) is equal to one in that interval. A segment of the ECG repolarization signal corresponding to the interval between the Twave onset and Twave offset is normalized so that the duration (x) is equal to one in that interval, FIG. 2.

The first and second derivatives of the ECG repolarization segment are determined on the interval between the Twave onset and Twave offset. The two derivative signals are subsequently used to calculate a radius of curvature (Rcurv) signal using equation 1. In one embodiment of the invention local maxima and local minima on the Rcurv signal between Twave onset (Tonset) and Twave offset (Toffset) are determined. The peak of the Twave (Tpeak) typically constitutes a local maximum of the Rcurv signal. The signal is analysed further to investigate if further maxima and minima exist. Any deflections on the Rcurv signal correspond to deviations from the normal, smooth progress of a T-wave. The Rcurv signal is normalized to get a maximum amplitude of 1. A notch or hump is reflected as a contiguous positive-negative pair on the Rcurv signal and when such a pair is present, a notch score is defined as the positive peak value of this pair. If no notches are present, the score is 0.

Figure 3:
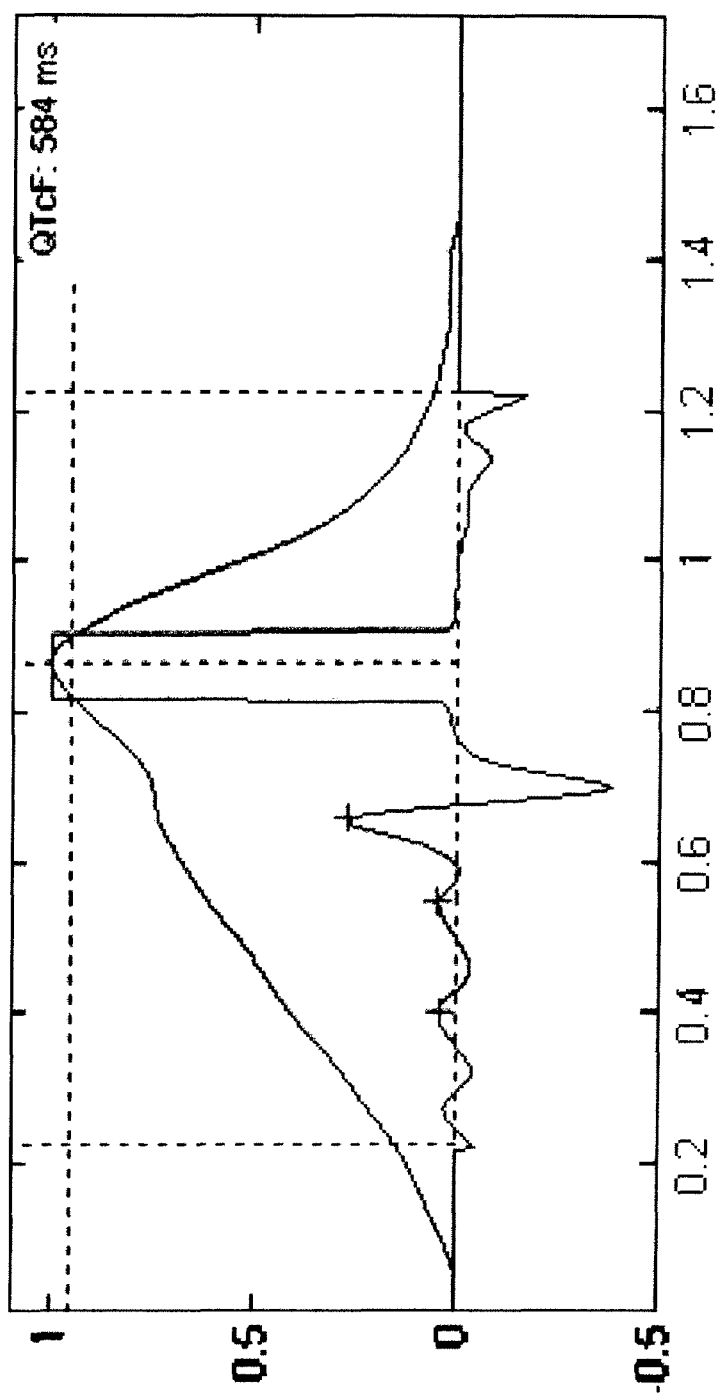
FIG. 3. Local maxima (LmRcurv) on the radius of curvature signal (Rcurv) indicated by red+marks. Values inside the Twave peak window on the Rcurv are set to equal one and are not used for further analysis.

In another embodiment for the invention, local maxima (LmRcurv) on the Rcurv signal between the Twave onset and Twave offset are determined, excluding LmRcurv points in a window symmetric around the Twave peak. The width of the window is set to twice the maximum duration of the return of Twave amplitude to 95% of the Tpeak value on either side of the Twave peak, or 20 ms, whichever is smaller. LmRcurv points with values below zero are also excluded as well as LmRcurv points, which correspond in time to ECG repolarization amplitudes below 40% of the maximum value of the normalized repolarization segment, FIG. 3.

Figure 4:
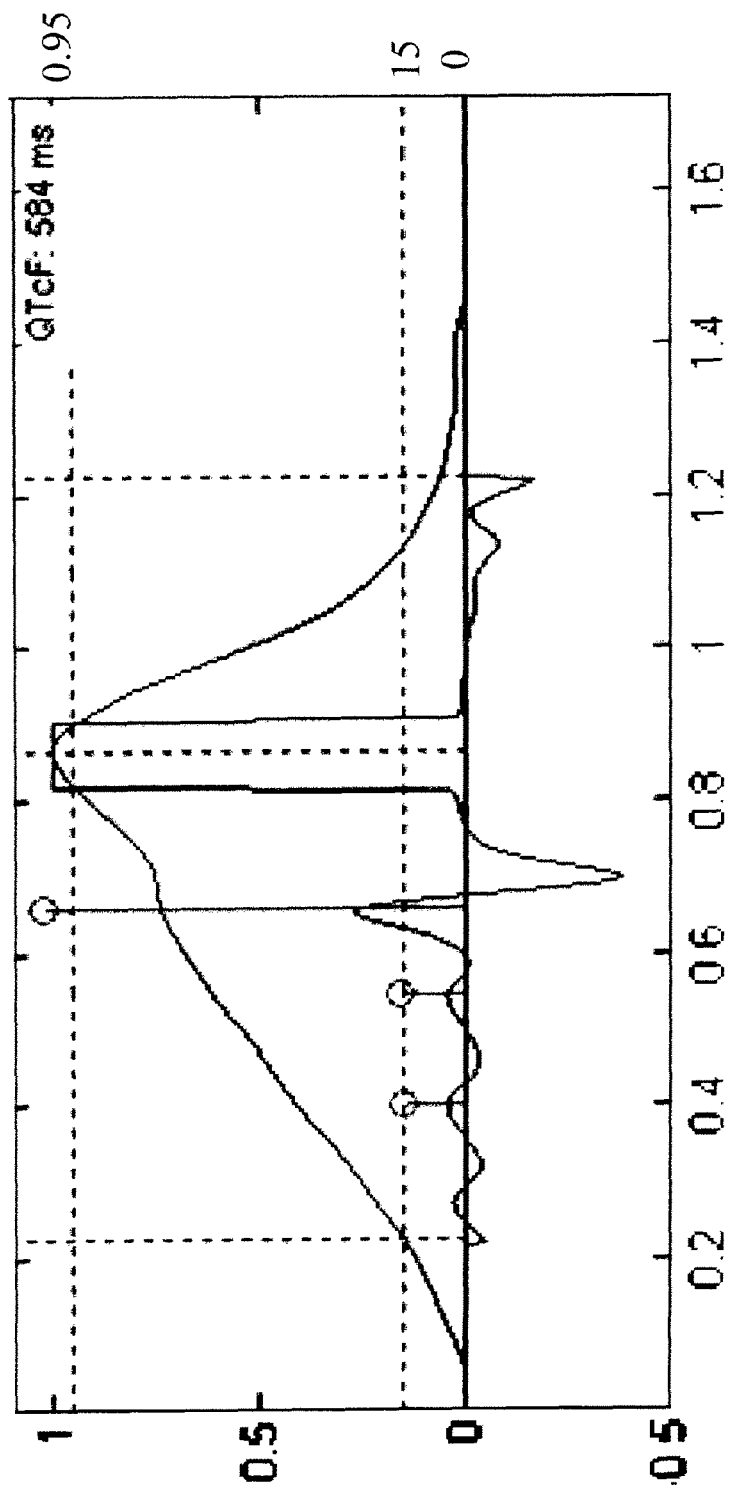
FIG. 4. Downwards concavity certainty measures (Cm) indicated by red stems.

The LmRcurv points that are left after exclusion according to the above given criteria are reference points. Positive segment durations on the Rcurv on either side of all reference points are multiplied by the value of the corresponding LmRcurv values to obtain certainty measures (Cm) of the presence of local downward concavities. Certainty measures exceeding a threshold of 15 ($Thr_{15}$) are defined as places around which concavity intervals are defined and local downward concavities are quantified, FIG. 4.

Figure 5:
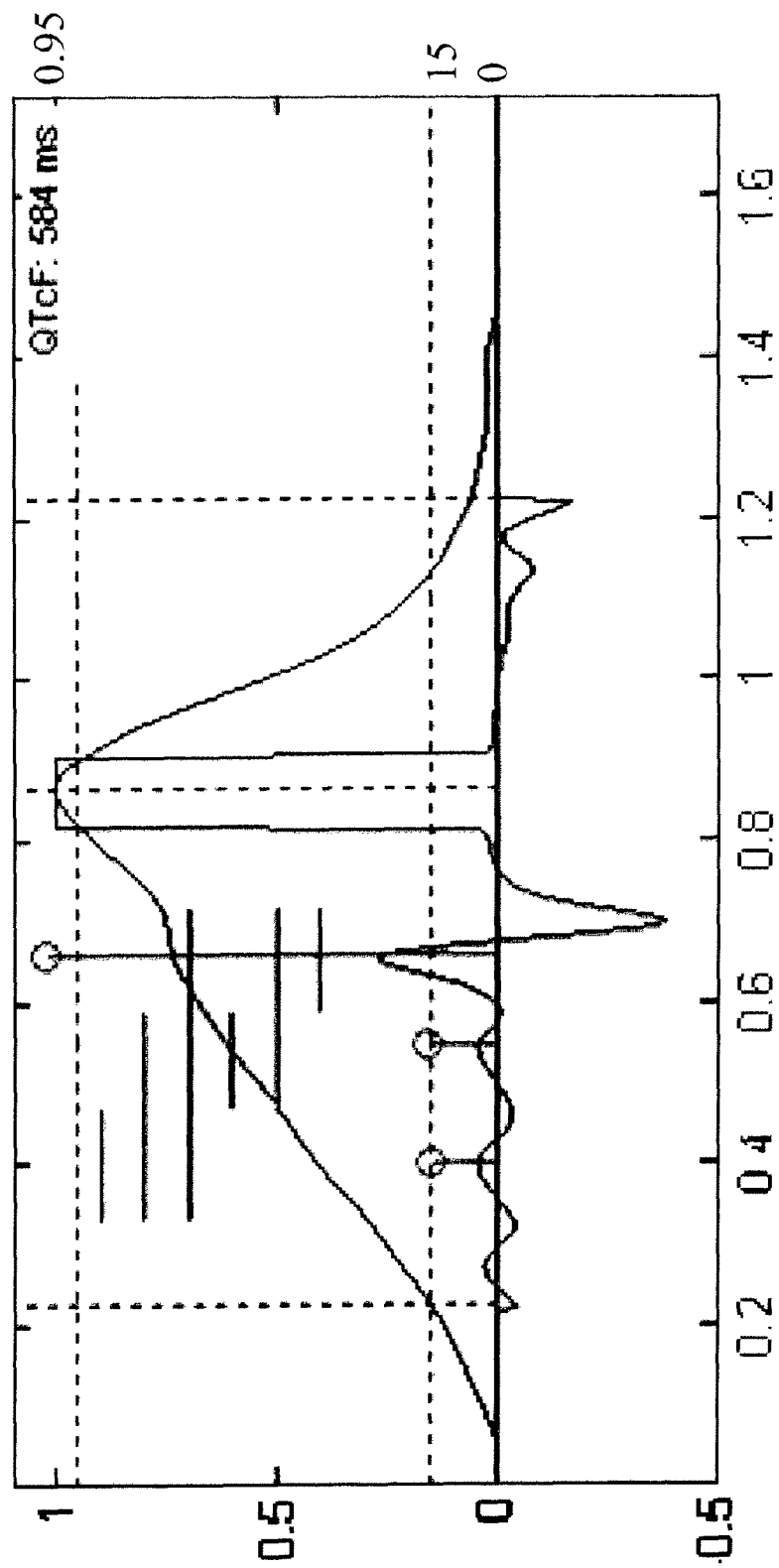
FIG. 5. shows concavity intervals around a certainty measure that given by all combinations of intervals between local maxima on the second derivative signal.

Concavity intervals around a certainty measure that exceeds $Thr_{15}$ are given by all combinations of intervals between local maxima on the second derivative signal, FIG. 5.

In the case when a certainty measure is not located between two local maxima on the second derivative signal, additional concavity interval combinations are made using the Twave onset, Twave offset or the first point outside the Twave peak window.

Figure 6:
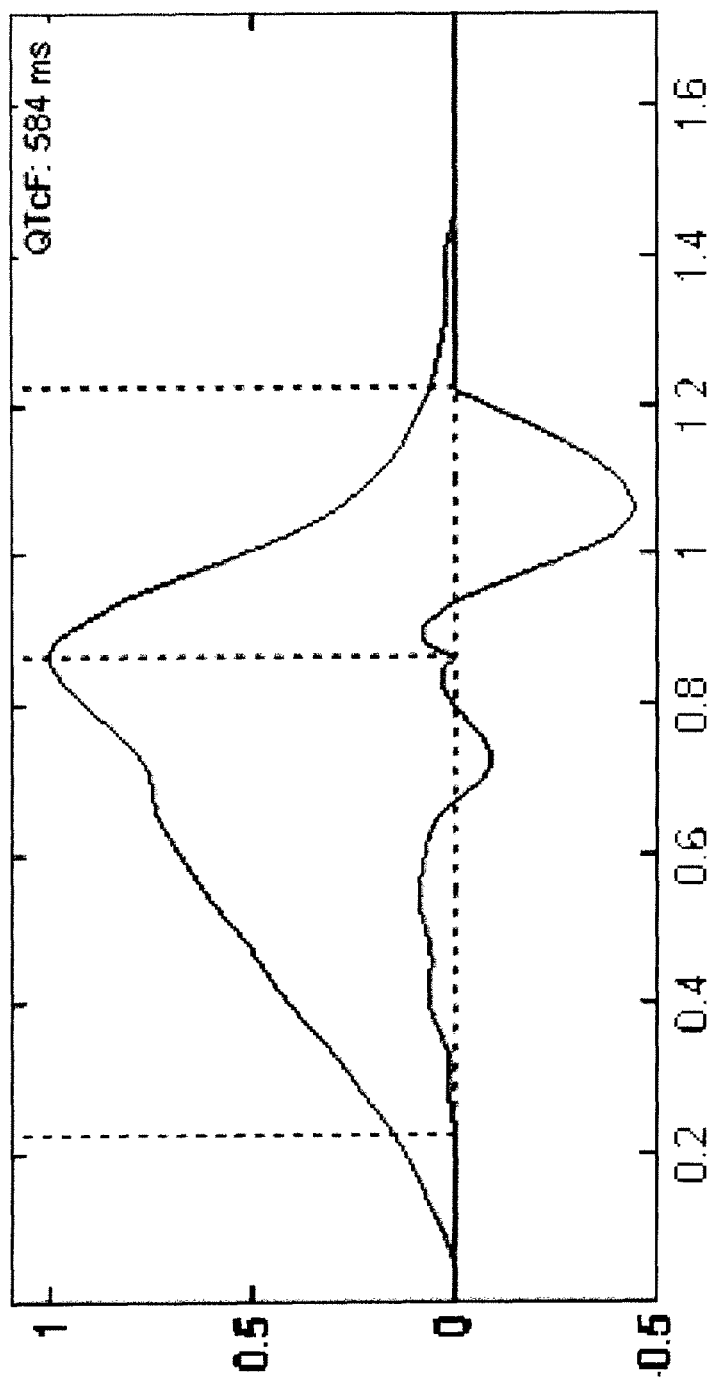
FIG. 6. Tilted subsegments $T_{1tilt}$ and $T_{2tilt}$.

The concavity intervals are evaluated on subsegments of the ECG repolarization segment and form the basis of downwards concavity quantification. Two piecewise tilted segments make up the subsegments. One tilted subsegment ($T_{1tilt}$) is given by the repolarization interval between the Twave onset and Twave peak from which the linear function between the two endpoints is subtracted. The other tilted subsegment ($T_{2tilt}$) is given by the repolarization interval between the Twave peak and Twave offset from which the linear function between the two endpoints is subtracted, FIG. 6.

Figure 7:
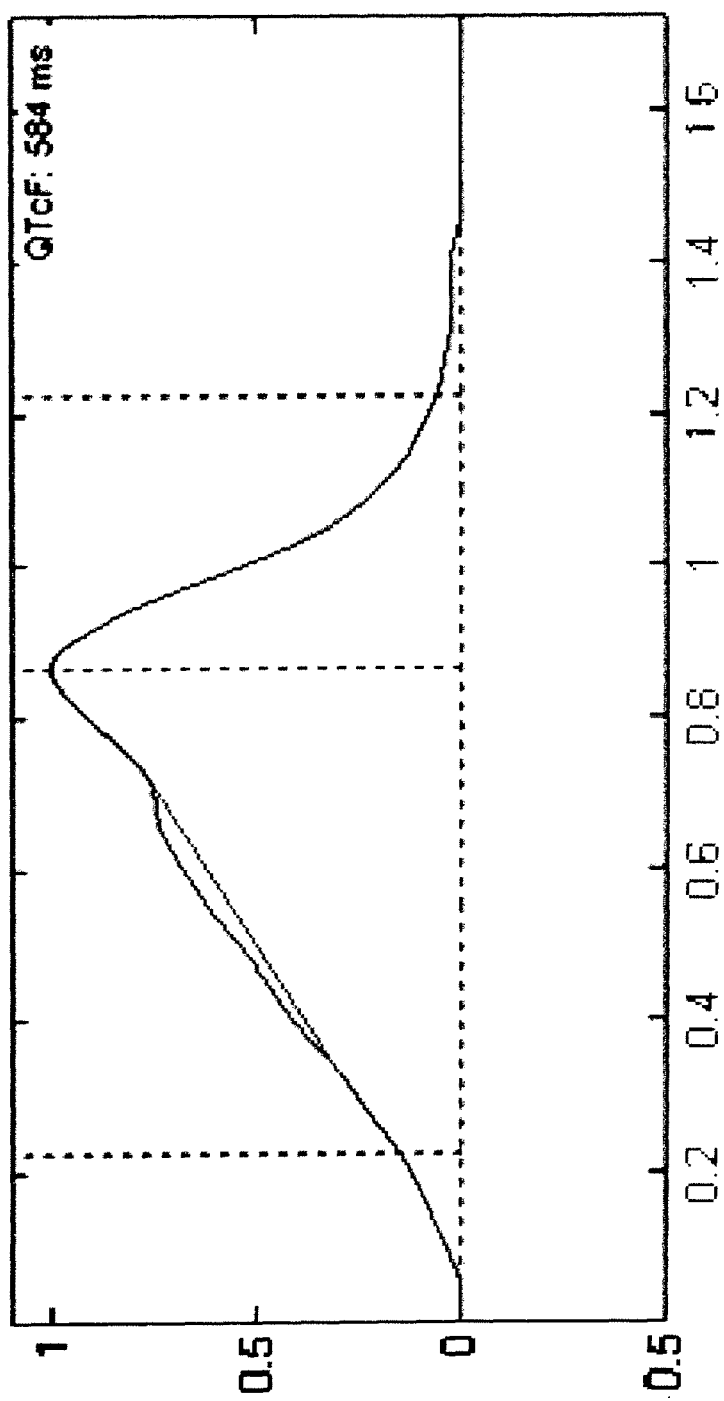
FIG. 7. Final maximum downwards concavity interval. Downwards concavity score (CdS) is given by the maximum difference between the angled line and the Twave FIG. 8. Concavity scores for the electrocardiographic lead V5

On both of the tilted subsegments all concavity intervals shown in FIG. 5 are evaluated and maximum values ($T_{1tiltmax}$ and $T_{2tiltmax}$) on the tilted subsegments in the concavity intervals are determined. The overall maximum value is the final concave down score (CdS) of the ECG repolarization segment given by equation 2 and shown indicated in FIG. 7.

$$CdS = \max([T_{1tilt\,max} T_{2tilt\,max}])\qquad\text{Equation 2}$$

On repolarization segments where no LmRcurv points are present or in case no LmRcurv points remain after the exclusion criteria, a upwards concavity score is calculated. The least negative maximum on either piecewise repolarization subsegment is used as an initial upwards concavity score (IuS). This score is then corrected in such a way as to obtain a final upwards concavity score (CuS) of zero when any certainty measure equals the certainty threshold and a final CuS score equal to IuS when no LmRcurv points remain after the exclusion criteria step. This relationship is given by equation 3.

$$CuS = IuS\left(1 - \frac{Cm}{Thr_{15}}\right)\qquad\text{Equation 3}$$

All positive concavity scores indicate the presence of a concave down curvature on the ECG repolarization signal. The magnitude of a positive CdS value reflects the extent of downwards concavity on an ECG repolarization segment. All negative concavity scores indicate that no significant downwards concave segments were identified on the ECG repolarization segment. The magnitude of a negative CuS value reflects the extent of upwards concavity on an ECG repolarization segment.

Figure 8:
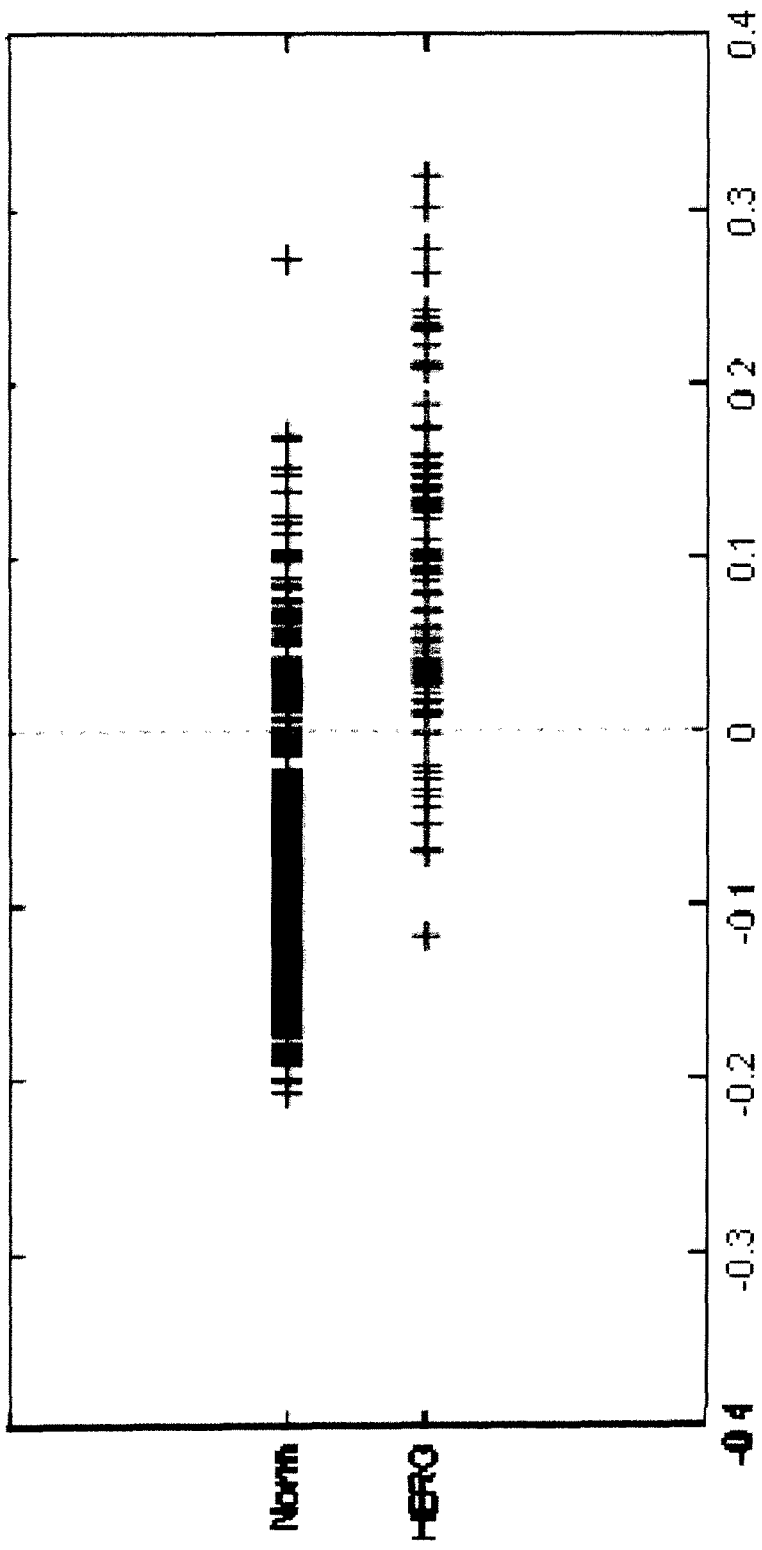
Figure 9:
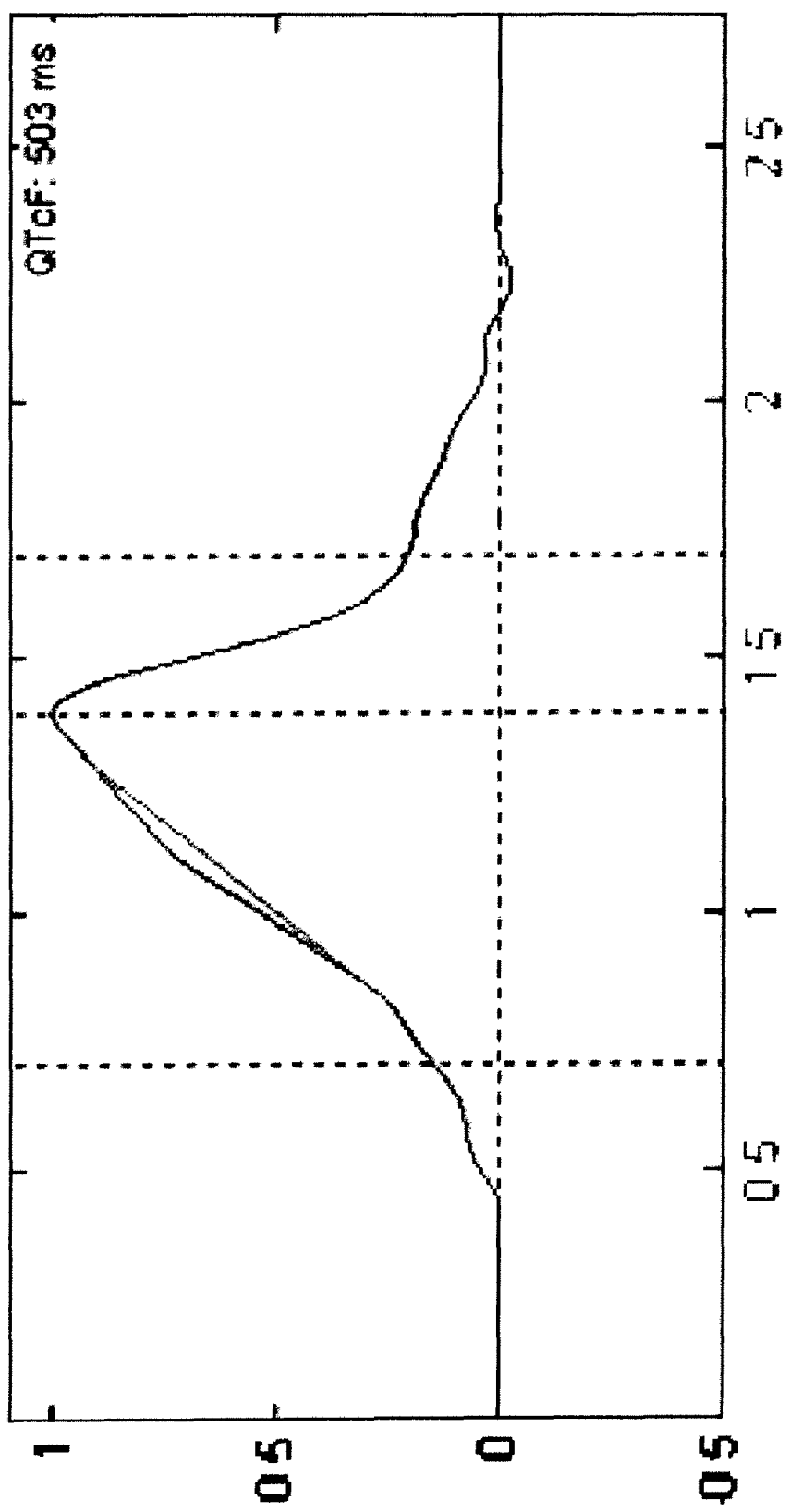
FIG. 9 Concave down curvature segment
Figure 10:
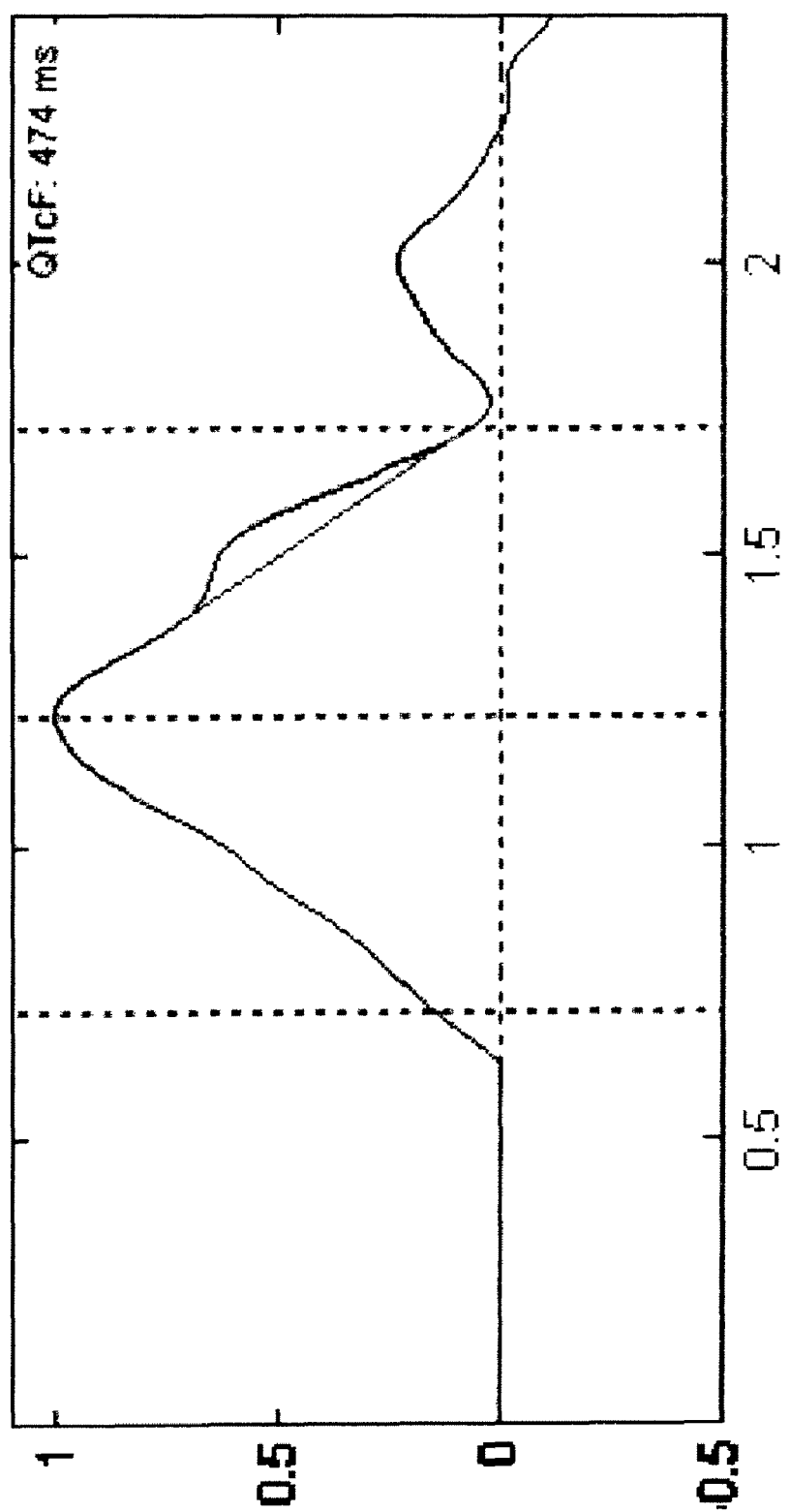
FIG. 10 Concave down curvature segment
FIG. 11 Concave down curvature segment
FIG. 12 Concave down curvature segment
FIG. 13 Concave down curvature segment
FIG. 14 Concave down curvature segment
FIG. 15 Concave down curvature segment
FIG. 16 Concave down curvature segment
FIG. 17 Concave down curvature segment
FIG. 18 Concave down curvature segment
FIG. 19 Concave down curvature segment
Figure 11:
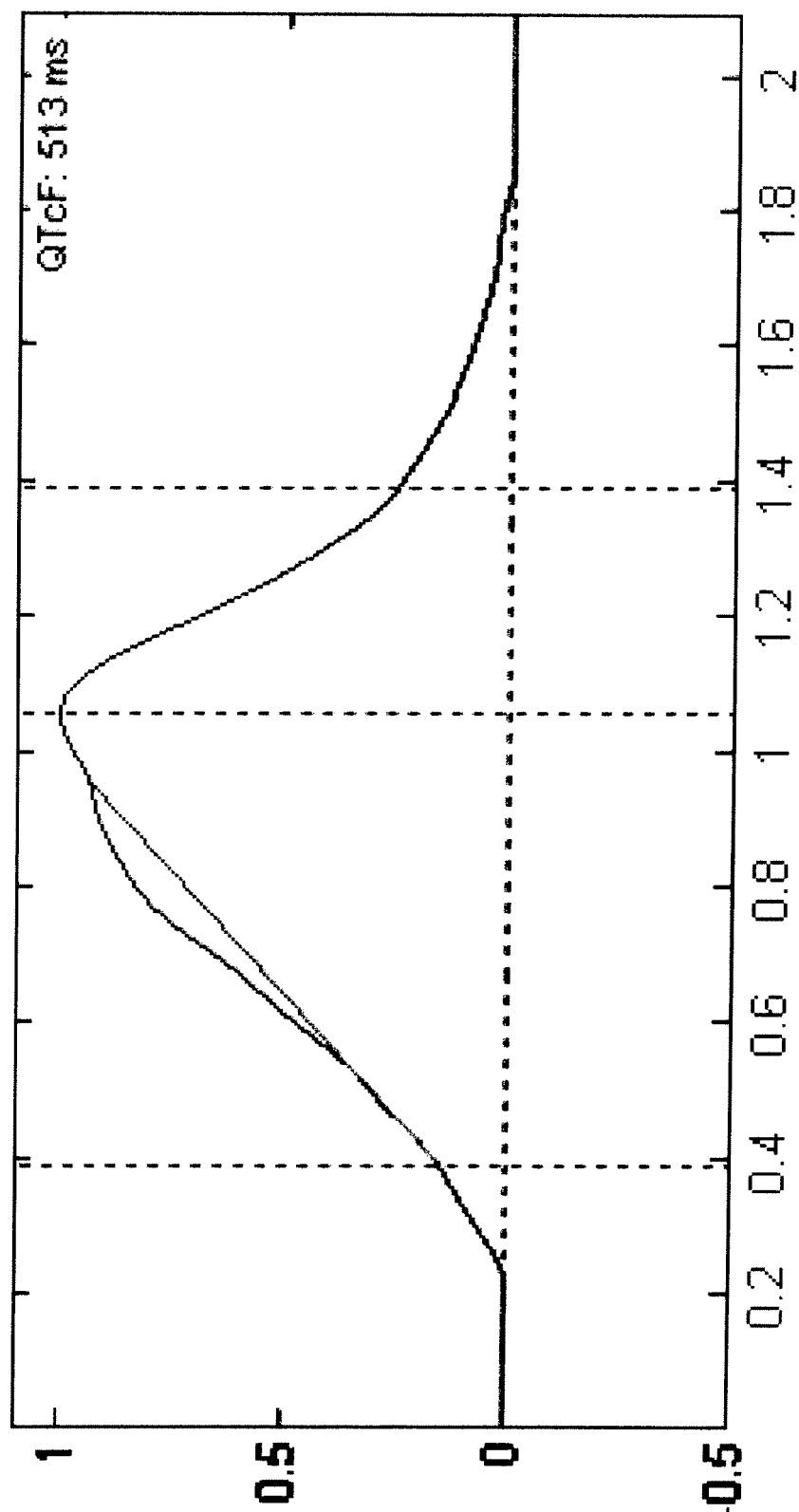
Figure 12:
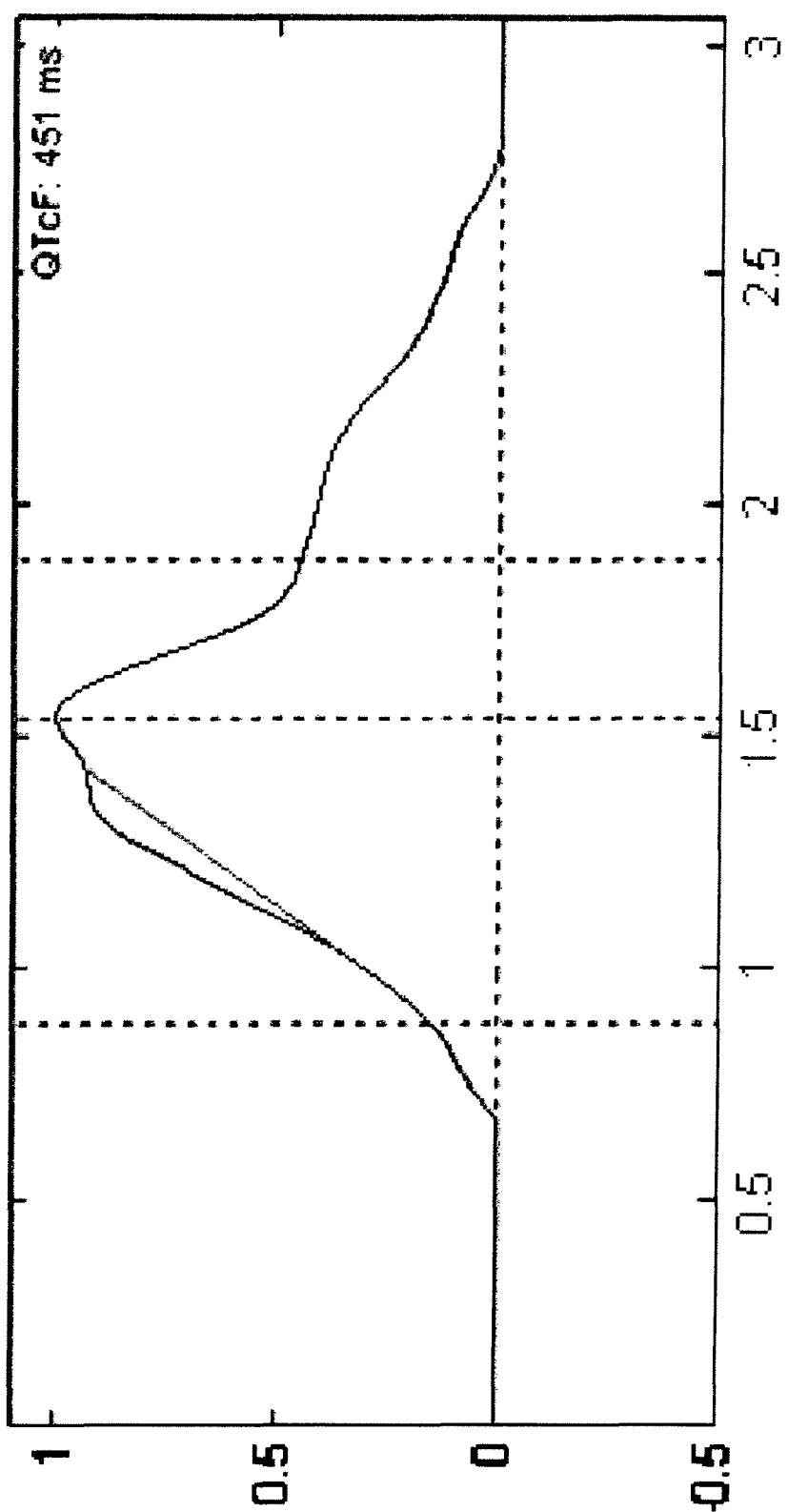
Figure 13:
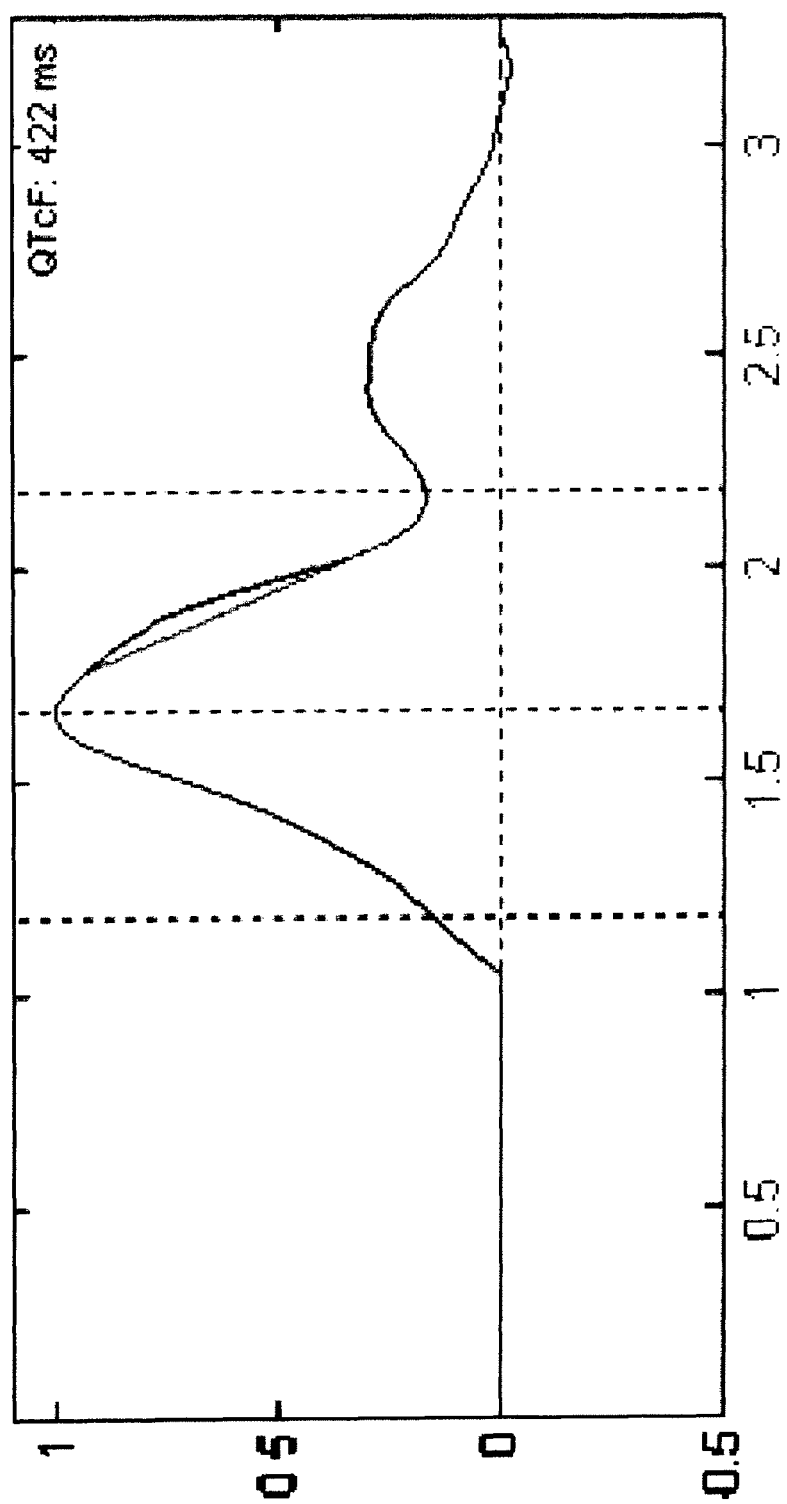
Figure 14:
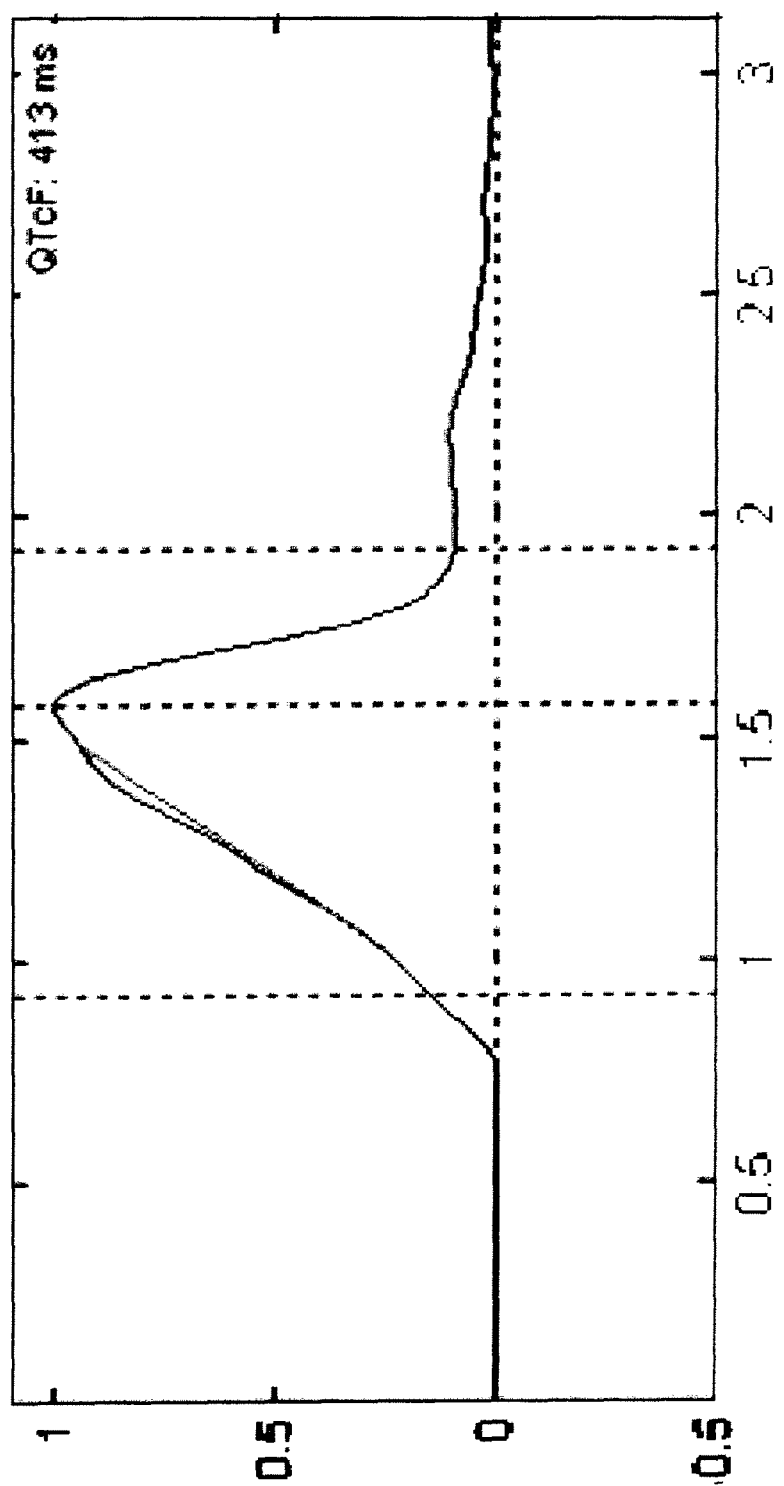
Figure 15:
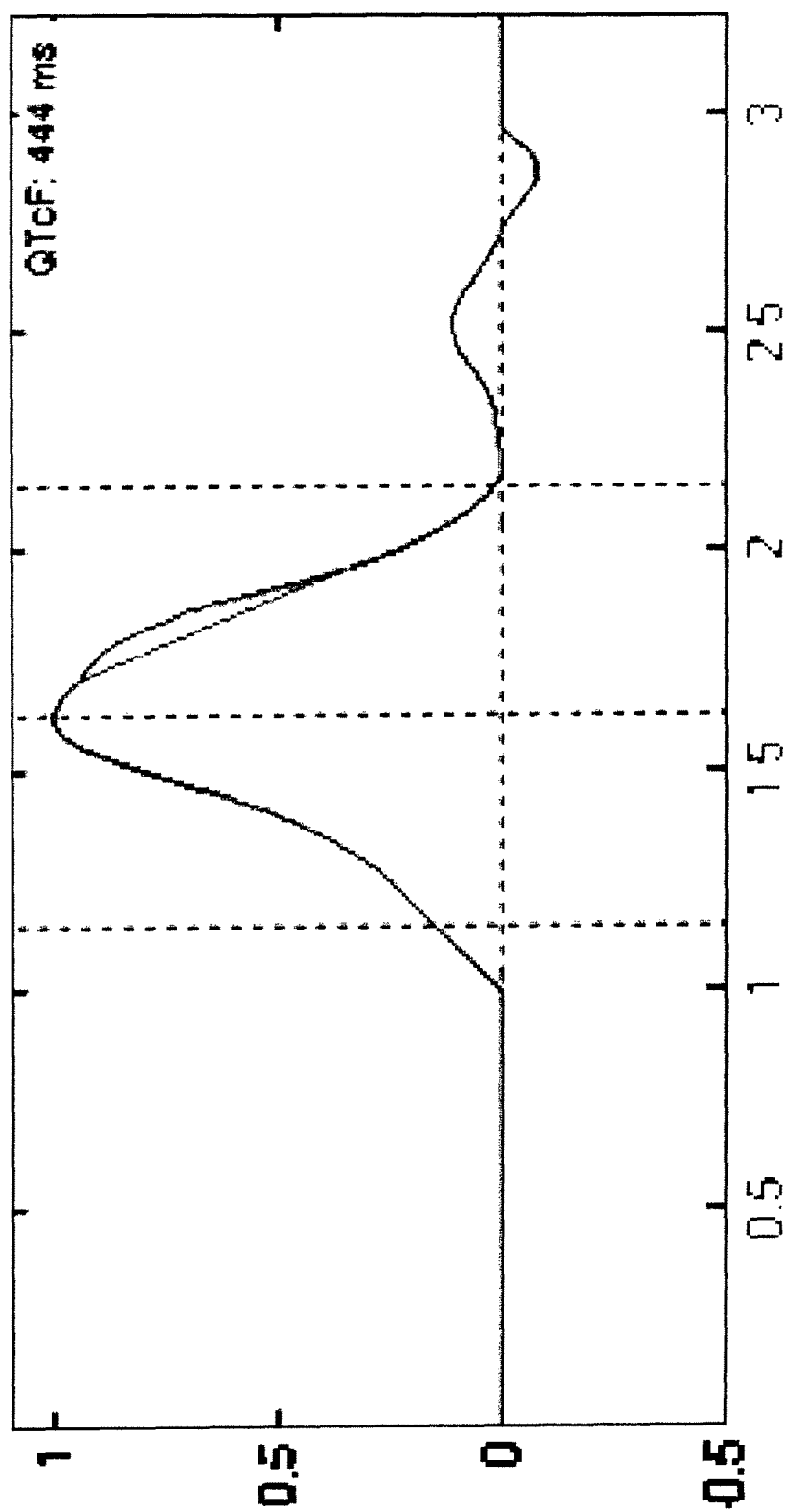
Figure 16:
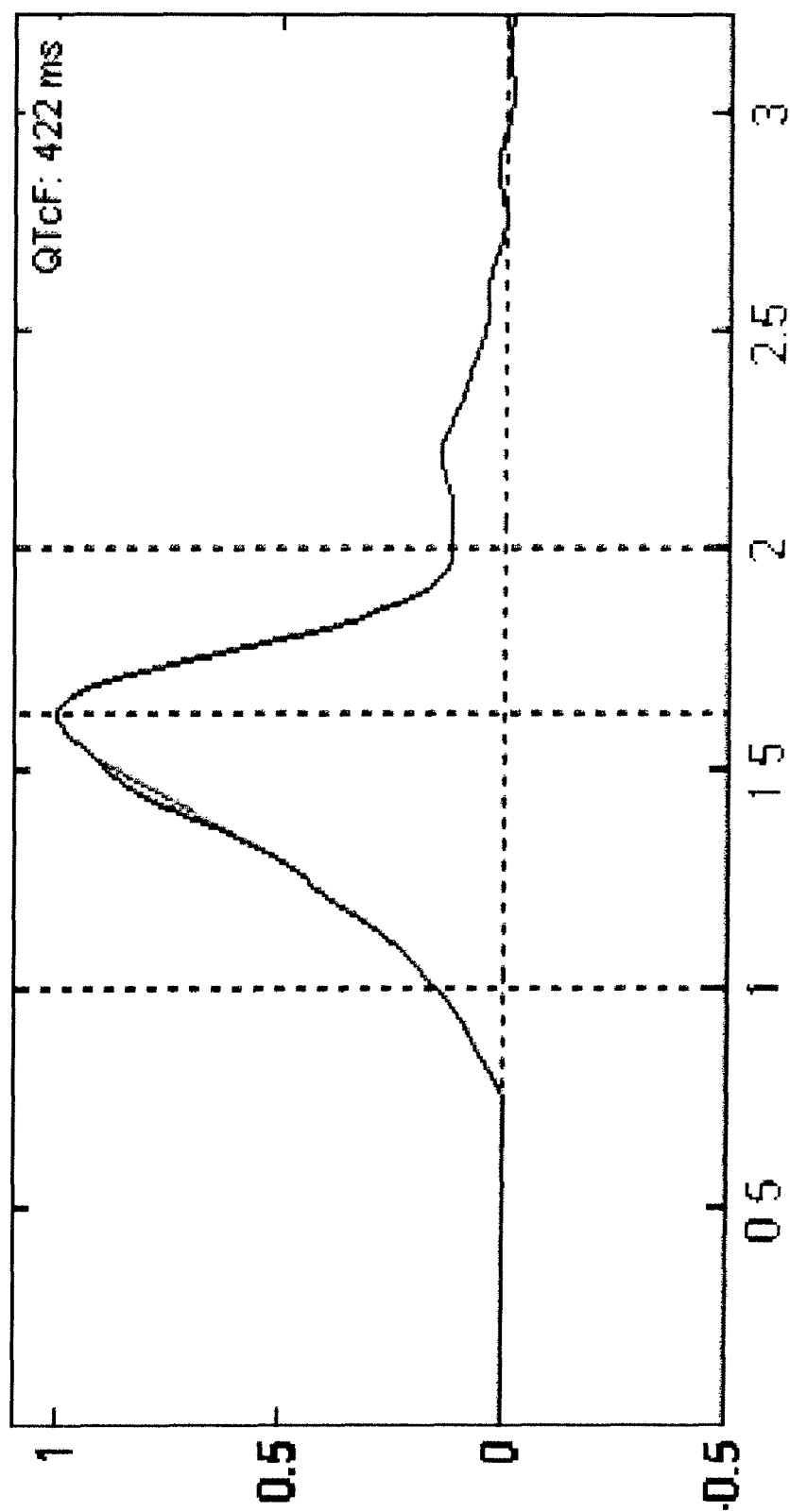
Figure 17:
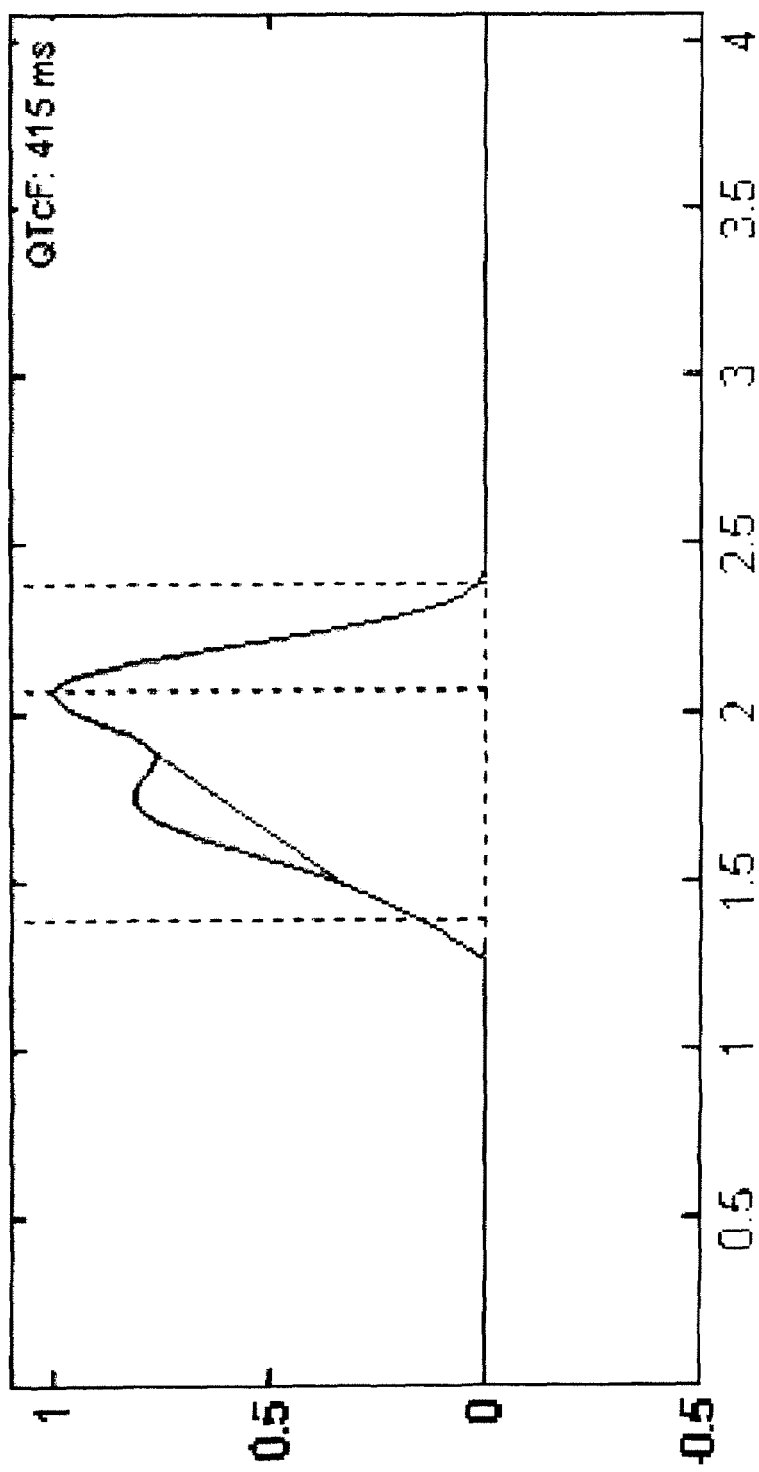
Figure 18:
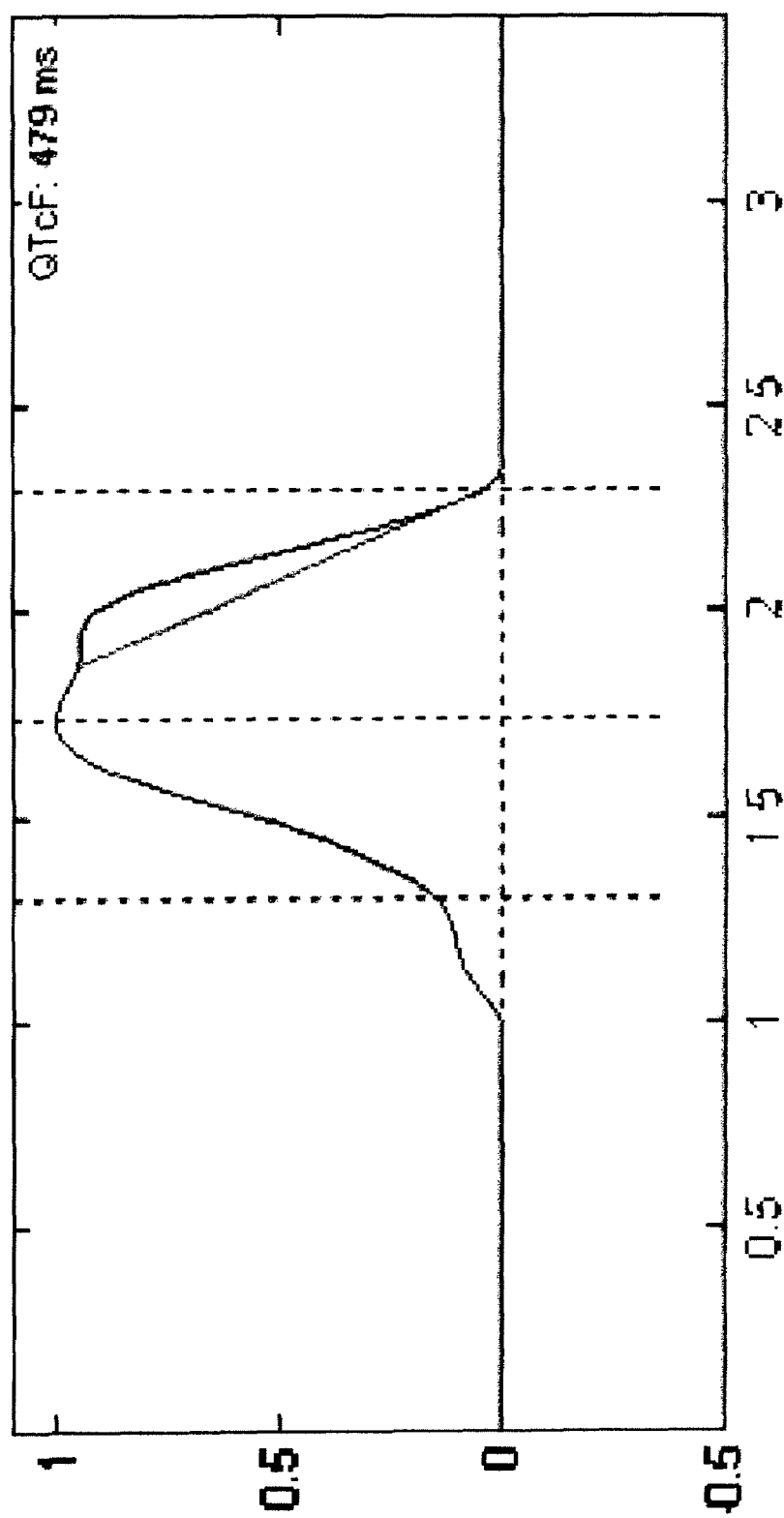

The method described above has been used to obtain concavity scores for 1093 ECG repolarization segments from verified healthy normal subjects and 117 ECG repolarization segments from genotyped congenital Long QT Syndrome subjects with mutations on the HERG gene. Concavity scores for a standard V5 lead are given in FIG. 8. Specificity and sensitivity for lead V5 were 93.6% and 89.4% respectively. Specificity and sensitivity using a composite lead were 95.8% and 83.8% respectively. The method has multiple application areas and may also be used to detect and quantify repolarization concavity in the acquired form of the Long QT syndrome and in patients with other electrocardiographic repolarization abnormalities FIGS. 9-18 show examples of various concave down curvatures detected and quantified by the algorithm.

Figure 19:
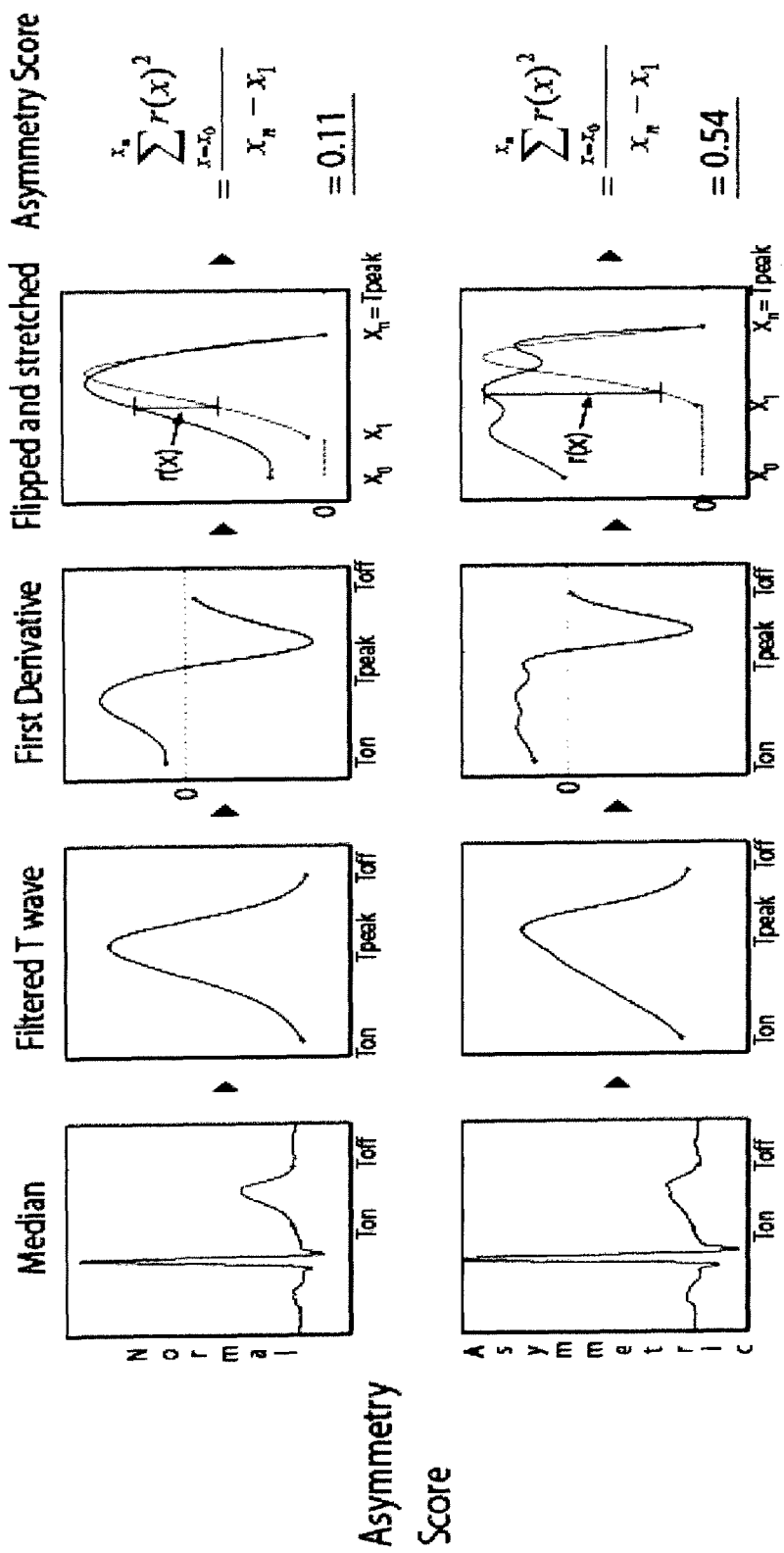

FIG. 19 shows the asymmetry score evaluates differences in slope profile and duration of the ascending and descending part of the T-wave. In one embodiment, the first derivative of the filtered T-wave is calculated and divided into two segments corresponding to ascending and descending T-wave. Both segments are normalized with the maximum amplitude of the first derivative within each segment. Then the descending T-wave segment is flipped across the y-axis and x-axis to cover the ascending segment. The segments are compared sample by sample, and the asymmetry score is the average residual between the two segments.

Figure 20:
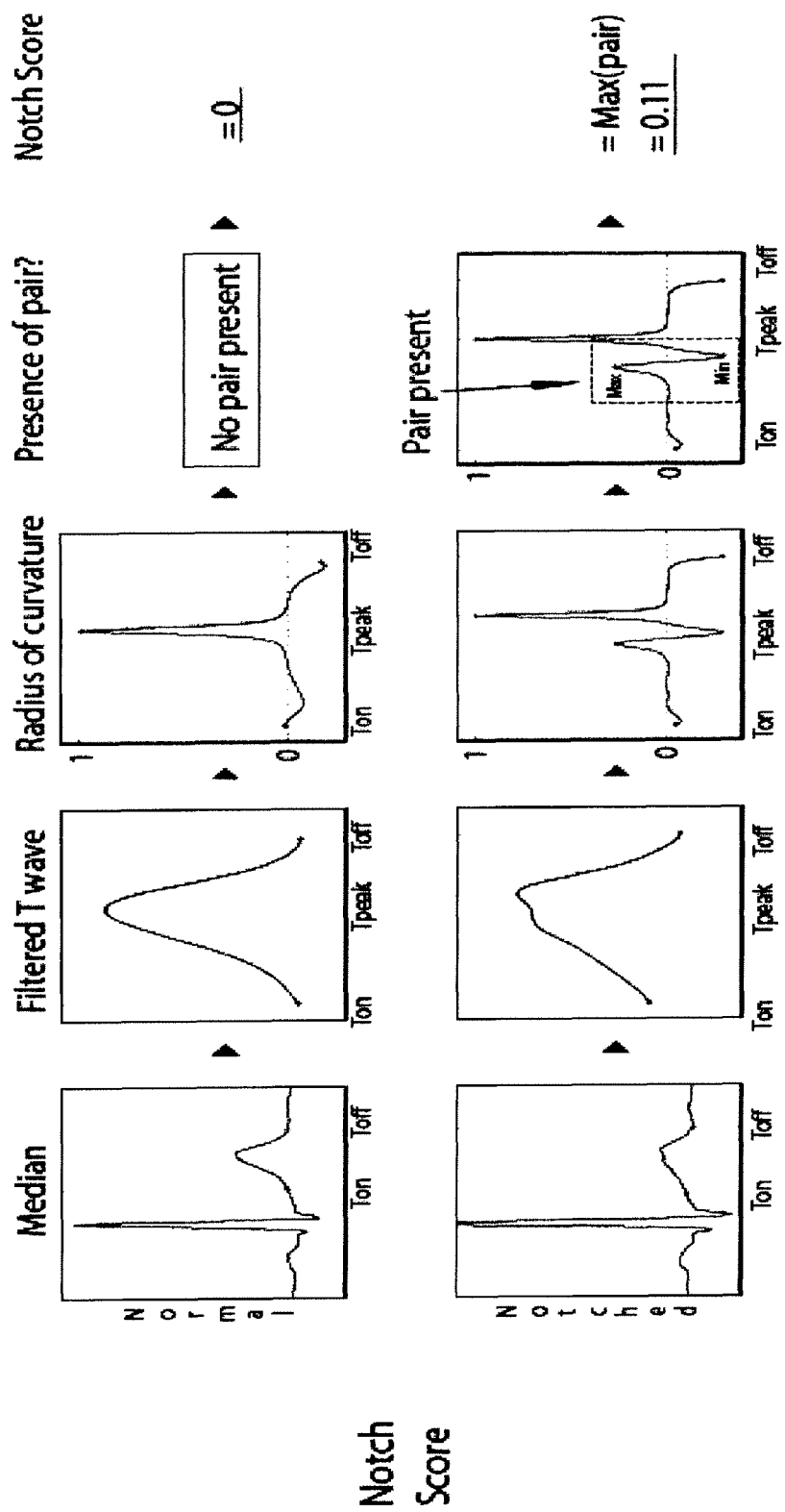
FIG. 20 shows the notch score reflects the size of any visible notches on the T-wave.

FIG. 20 shows the notch score reflects the size of any visible notches on the T-wave. In one embodiment, the score is obtained from the inverse, signed radius of curvature (Rcurv) of the T-wave. Any deflections on this signal correspond to deviations from the normal, smooth progress of a T-wave. The Rcurv signal is normalized to get a maximum amplitude of 1. A true notch is reflected as an up-down pair on the Rcurv signal and when such a pair is present, the notch score is defined as the positive peak value of this pair. If no notches are present, the score is 0.

1.4 Peak_Curvature

The peakedness of the T wave peak (Peak_Curvature) is evaluated by calculating the radius of curvature value (Rcurv) in Tpeak.

The radius of curvature is given by:

$$Rcurv = -\frac{\left[1 + \left(\frac{dy}{dx}\right)^2\right]^{3/2}}{\frac{d^2y}{dx^2}},$$

where x is the timescale normalized with the T wave width, and y is the ECG signal normalized with the T wave amplitude.

1.5 Symmetry Residual

The symmetric properties of the T wave are evaluated by comparing the T wave curve on the right side of Tpeak with the T wave curve on the left side of Tpeak.

The comparison of left and right side is done on any representation of the T wave, such as the time domain ECG signal, the first derivative of the signal, the second derivative of the signal or any combination of these such as the radius of curvature of the signal (Rcurv as described above).

The Twave representation of the right side of Tpeak is flipped around a vertical line through Tpeak to cover the left side of Tpeak. If first or second derivative is used, the Twave representation of the right side of Tpeak is also flipped around the x axis to compensate for the sign difference between the two sides.

If the lengths of the two representations (left side and flipped right side) differ, this is corrected either by resampling each side to a common length or by zero-padding the shortest side to fit the length of the other.

Prior to the comparison the two representations can be normalized with their respective amplitude to give a better fit.

The two representations are now compared sample by sample. A residual is calculated by evaluating the summed sample-by-sample difference between the two representations. The difference can be absolute or squared before summing.

The total residual is a reliable measure of the symmetry of T wave.

1.6 Parameter Description

Symmetry

S1 Skewness evaluated in a symmetric interval, 30% of the Tstart-Tend interval, surrounding Tpeak with Tpeak as mean S2 Skewness evaluated in a symmetric interval, 40% of the Tstart-Tend interval, surrounding Tpeak with Tpeak as mean S3 Skewness evaluated in a symmetric interval, 50% of the Tstart-Tend interval, surrounding Tpeak with Tpeak as mean S4 Skewness evaluated in a symmetric interval, 60% of the Tstart-Tend interval, surrounding Tpeak with Tpeak as mean S5 Skewness evaluated in a symmetric interval, 70% of the Tstart-Tend interval, surrounding Tpeak with Tpeak as mean S6 Skewness evaluated in a symmetric interval, 80% of the Tstart-Tend interval, surrounding Tpeak with Tpeak as mean S7 Skewness evaluated in a symmetric interval, 90% of the Tstart-Tend interval, surrounding Tpeak with Tpeak as mean S8 Skewness evaluated in a symmetric interval, 100% of the Tstart-Tend interval, surrounding Tpeak with Tpeak as mean S9 Skewness evaluated from Tstart toTend S10 Skewness evaluated in a symmetric interval, 10% of the Tstart-Tend interval, surrounding Center of Mass (CoM)

S11 Skewness evaluated in a symmetric interval, 20% of the Tstart-Tend interval, surrounding Center of Mass (CoM)

S12 Skewness evaluated in a symmetric interval, 30% of the Tstart-Tend interval, surrounding Center of Mass (CoM)

S13 Skewness evaluated in a symmetric interval, 40% of the Tstart-Tend interval, surrounding Center of Mass (CoM)

S14 Skewness evaluated in a symmetric interval, 50% of the Tstart-Tend interval, surrounding Center of Mass (CoM)

S15 Skewness evaluated in a symmetric interval, 60% of the Tstart-Tend interval, surrounding Center of Mass (CoM)

S16 Skewness evaluated in a symmetric interval, 70% of the Tstart-Tend interval, surrounding Center of Mass (CoM)

S17 Skewness evaluated in a symmetric interval, 80% of the Tstart-Tend interval, surrounding Center of Mass (CoM)

S18 Skewness evaluated in a symmetric interval, 90% of the Tstart-Tend interval, surrounding Center of Mass (CoM)

S19 Skewness evaluated in a symmetric interval, 100% of the Tstart-Tend interval, surrounding Center of Mass (CoM)

S20 Skewness evaluated in a asymmetric interval, with Tstart at 2% of the area from the j-point to Tend, and Tend at 98% of the area.

S21 Skewness evaluated in a asymmetric interval, with Tstart at 5% of the area from the j-point to Tend, and Tend at 95% of the area.

S22 Skewness evaluated in a asymmetric interval, with Tstart at 2% of the area from the j-point to Tpeak, and Tend at 98% of the area from Tpeak to Tend.

S23 Skewness evaluated in a asymmetric interval, with Tstart at 5% of the area from the j-point to Tpeak, and Tend at 95% of the area from Tpeak to Tend.

S24 Skewness evaluated in a asymmetric interval, with Tstart at 2% of the area from the j-point to CoM, and Tend at 98% of the area from CoM to Tend.

S25 Skewness evaluated in a asymmetric interval, with Tstart at 5% of the area from the j-point to CoM, and Tend at 95% of the area from CoM to Tend.

S26 Skewness evaluated in a asymmetric interval, which on the left side of Center of Mass(CoM) consist of, 10% of the Tstart-TCoM interval, and on the right side 10% of the TCoM-Tend interval S27 Skewness evaluated in a asymmetric interval, which on the left side of Center of Mass(CoM) consist of, 20% of the Tstart-TCoM interval, and on the right side 20% of the TCoM-Tend interval S28 Skewness evaluated in a asymmetric interval, which on the left side of Center of Mass(CoM) consist of, 30% of the Tstart-TCoM interval, and on the right side 30% of the TCoM-Tend interval S29 Skewness evaluated in a asymmetric interval, which on the left side of Center of Mass(CoM) consist of, 40% of the Tstart-TCoM interval, and on the right side 40% of the TCoM-Tend interval S30 Skewness evaluated in a asymmetric interval, which on the left side of Center of Mass(CoM) consist of, 50% of the Tstart-TCoM interval, and on the right side 50% of the TCoM-Tend interval S31 Skewness evaluated in a asymmetric interval, which on the left side of Center of Mass(CoM) consist of, 60% of the Tstart-TCoM interval, and on the right side 60% of the TCoM-Tend interval S32 Skewness evaluated in a asymmetric interval, which on the left side of Center of Mass(CoM) consist of, 70% of the Tstart-TCoM interval, and on the right side 70% of the TCoM-Tend interval S33 Skewness evaluated in a asymmetric interval, which on the left side of Center of Mass(CoM) consist of, 80% of the Tstart-TCoM interval, and on the right side 80% of the TCoM-Tend interval S34 Skewness evaluated in a asymmetric interval, which on the left side of Center of Mass(CoM) consist of, 80% of the Tstart-TCoM interval, and on the right side 90% of the TCoM-Tend interval S35 Skewness evaluated in a asymmetric interval, which on the left side of Center of Mass(CoM) consist of, 100% of the Tstart-TCoM interval, and on the right side 100% of the TCoM-Tend interval S36 Skewness evaluated in a asymmetric interval, which on the left side of Tpeak consist of, 10% of the Tstart-TPeak interval, and on the right side 10% of the TPeak-Tend interval S37 Skewness evaluated in a asymmetric interval, which on the left side of Tpeak consist of, 20% of the Tstart-TPeak interval, and on the right side 20% of the TPeak-Tend interval S38 Skewness evaluated in a asymmetric interval, which on the left side of Tpeak consist of, 30% of the Tstart-TPeak interval, and on the right side 30% of the TPeak-Tend interval S39 Skewness evaluated in a asymmetric interval, which on the left side of Tpeak consist of, 40% of the Tstart-TPeak interval, and on the right side 40% of the TPeak-Tend interval S40 Skewness evaluated in a asymmetric interval, which on the left side of Tpeak consist of, 50% of the Tstart-TPeak interval, and on the right side 50% of the TPeak-Tend interval S41 Skewness evaluated in a asymmetric interval, which on the left side of Tpeak consist of, 60% of the Tstart-TPeak interval, and on the right side 60% of the TPeak-Tend interval S42 Skewness evaluated in a asymmetric interval, which on the left side of Tpeak consist of, 70% of the Tstart-TPeak interval, and on the right side 70% of the TPeak-Tend interval S43 Skewness evaluated in a asymmetric interval, which on the left side of Tpeak consist of, 80% of the Tstart-TPeak interval, and on the right side 80% of the TPeak-Tend interval S44 Skewness evaluated in a asymmetric interval, which on the left side of Tpeak consist of, 90% of the Tstart-TPeak interval, and on the right side 90% of the TPeak-Tend interval S45 Skewness evaluated in a asymmetric interval, which on the left side of Tpeak consist of, 100% of the Tstart-TPeak interval, and on the right side 100% of the TPeak-Tend interval S46 Symmetry parameters, S1-S45, normalized by the size of the QRS amplitude S47 The area of the T-wave calculated in the interval from Tstart to Tend S48 Symmetry parameter, S47, normalized by the size of the QRS amplitude.

S49 The area of the T-wave calculated in the interval from Tpeak to Tend

S50 Symmetry parameter, S49, normalized by the size of the QRS amplitude.

S51 The area of the T-wave calculated in the interval from Tstart to TPeak

S52 Symmetry parameter, S51, normalized by the size of the QRS amplitude.

S53 Ratio of the area calculated in the interval from Tstart to Tpeak and the area calculated in the interval from Tpeak to Tend.

S54 Ratio of the total area of the Twave and the tail area, where the tail area in the case that the duration of Tstart-Tpeak>duration of Tpeak-Tend, is the area in the interval from Tstart to Tpeak−(Tend−Tpeak), and vice versa.

S55 Symmetry residual of the Twave parts, respectively from Tstart-Tpeak and Tpeak-Tend S56 Symmetry residual of the first derivative of the Twave parts, respectively from Tstart-Tpeak and Tpeak-Tend S57 Symmetry residual of the second derivative of the Twave parts, respectively from Tstart-Tpeak and Tpeak-Tend S58 Symmetry parameter, S55, normalizing the interval Tstart-Tpeak and Tpeak-Tend by resampling both.

S59 Symmetry parameter, S55, normalizing the interval Tstart-Tpeak and Tpeak-Tend by zero padding the interval with the shortest duration S60 Symmetry parameter, S56, normalizing the interval Tstart-Tpeak and Tpeak-Tend by resampling both.

S61 Symmetry parameter, S56, normalizing the interval Tstart-Tpeak and Tpeak-Tend by zero padding the interval with the shortest duration S62 Symmetry parameter, S57, normalizing the interval Tstart-Tpeak and Tpeak-Tend by resampling both.

S63 Symmetry parameter, S57, normalizing the interval Tstart-Tpeak and Tpeak-Tend by zero padding the interval with the shortest duration S64 Symmetry parameter, S55, normalized by their respective amplitude S65 Symmetry parameter, S56, normalized by their respective amplitude S66 Symmetry parameter, S57, normalized by their respective amplitude S67 Symmetry parameter, S58, normalized by their respective amplitude S68 Symmetry parameter, S59, normalized by their respective amplitude S69 Symmetry parameter, S60, normalized by their respective amplitude S70 Symmetry parameter, S61, normalized by their respective amplitude S71 Symmetry parameter, S62, normalized by their respective amplitude S72 Symmetry parameter, S63, normalized by their respective amplitude Flatness
- F1 Flatness with Tpeak as mean evaluated in a symmetric interval of 30% of the Tstart-Tend interval surrounding Tpeak.
- F2 Flatness parameter, F1, normalized by the size of the QRS amplitude.
- F3 Flatness with Tpeak as mean evaluated in a symmetric interval of 40% of the Tstart-Tend interval surrounding Tpeak.
- F4 Flatness parameter, F3, normalized by the size of the QRS amplitude.
- F5 Flatness with Tpeak as mean evaluated in a symmetric interval of 50% of the Tstart-Tend interval surrounding Tpeak.
- F6 Flatness parameter, F5, normalized by the size of the QRS amplitude.
- F7 Flatness with Tpeak as mean evaluated in a symmetric interval of 60% of the Tstart-Tend interval surrounding Tpeak.
- F8 Flatness parameter, F7, normalized by the size of the QRS amplitude.
- F9 Flatness with Tpeak as mean evaluated in a symmetric interval of 70% of the Tstart-Tend interval surrounding Tpeak.
- F10 Flatness parameter, F9, normalized by the size of the QRS amplitude.
- F11 Flatness with Tpeak as mean evaluated in a symmetric interval of 80% of the Tstart-Tend interval surrounding Tpeak.
- F12 Flatness parameter, F11, normalized by the size of the QRS amplitude.
- F13 Flatness with Tpeak as mean evaluated in a symmetric interval of 90% of the Tstart-Tend interval surrounding Tpeak.
- F14 F14 Flatness parameter, F13, normalized by the size of the QRS amplitude.
- F15 Flatness with Tpeak as mean evaluated in a symmetric interval of 100% of the Tstart-Tend interval surrounding Tpeak.
- F16 Flatness parameter, F15, normalized by the size of the QRS amplitude.
- F17 Flatness with Tpeak as mean from Tstart to Tend
- F18 Flatness parameter, F17, normalized by the size of the QRS amplitude.
- F19 Flatness evaluated in a symmetric interval of 10% of the Tstart-Tend interval surrounding Center of Mass (CoM)
- F20 Flatness parameter, F19, normalized by the size of the QRS amplitude
- F21 Flatness evaluated in a symmetric interval of 20% of the Tstart-Tend interval surrounding Center of Mass (CoM)
- F22 Flatness parameter, F21, normalized by the size of the QRS amplitude
- F23 Flatness evaluated in a symmetric interval of 30% of the Tstart-Tend interval surrounding Center of Mass (CoM)
- F24 Flatness parameter, F23, normalized by the size of the QRS amplitude
- F25 Flatness evaluated in a symmetric interval of 40% of the Tstart-Tend interval surrounding Center of Mass (CoM)
- F26 Flatness parameter, F25, normalized by the size of the QRS amplitude
- F27 Flatness evaluated in a symmetric interval of 50% of the Tstart-Tend interval surrounding Center of Mass (CoM)
- F28 Flatness parameter, F27, normalized by the size of the QRS amplitude
- F29 Flatness evaluated in a symmetric interval of 60% of the Tstart-Tend interval surrounding Center of Mass (CoM)
- F30 Flatness parameter, F29, normalized by the size of the QRS amplitude
- F31 Flatness evaluated in a symmetric interval of 70% of the Tstart-Tend interval surrounding Center of Mass (CoM)
- F32 Flatness parameter, F31, normalized by the size of the QRS amplitude
- F33 Flatness evaluated in a symmetric interval of 80% of the Tstart-Tend interval surrounding Center of Mass (CoM)
- F34 Flatness parameter, F33, normalized by the size of the QRS amplitude
- F35 Flatness evaluated in a symmetric interval of 90% of the Tstart-Tend interval surrounding Center of Mass (CoM)
- F36 Flatness parameter, F35, normalized by the size of the QRS amplitude
- F37 Flatness evaluated in a symmetric interval of 100% of the Tstart-Tend interval surrounding Center of Mass (CoM)
- F38 Flatness parameter, F37, normalized by the size of the QRS amplitude
- F39 Flatness evaluated in a asymmetric interval, which on the left side of Tpeak consist of, 10% of the Tstart-TPeak interval, and on the right side 10% of the TPeak-Tend interval
- F40 Flatness parameter, F39, normalized by the size of the QRS amplitude
- F41 Flatness evaluated in a asymmetric interval, which on the left side of Tpeak consist of, 20% of the Tstart-TPeak interval, and on the right side 20% of the TPeak-Tend interval
- F42 Flatness parameter, F41, normalized by the size of the QRS amplitude
- F43 Flatness evaluated in a asymmetric interval, which on the left side of Tpeak consist of, 30% of the Tstart-TPeak interval, and on the right side 30% of the TPeak-Tend interval
- F44 Flatness parameter, F43, normalized by the size of the QRS amplitude
- F45 Flatness evaluated in a asymmetric interval, which on the left side of Tpeak consist of, 40% of the Tstart-TPeak interval, and on the right side 40% of the TPeak-Tend interval
- F46 Flatness parameter, F45, normalized by the size of the QRS amplitude
- F47 Flatness evaluated in a asymmetric interval, which on the left side of Tpeak consist of, 50% of the Tstart-TPeak interval, and on the right side 50% of the TPeak-Tend interval
- F48 Flatness parameter, F47, normalized by the size of the QRS amplitude
- F49 Flatness evaluated in a asymmetric interval, which on the left side of Tpeak consist of, 60% of the Tstart-TPeak interval, and on the right side 60% of the TPeak-Tend interval
- F50 Flatness parameter, F49, normalized by the size of the QRS amplitude
- F51 Flatness evaluated in a asymmetric interval, which on the left side of Tpeak consist of, 70% of the Tstart-TPeak interval, and on the right side 70% of the TPeak-Tend interval F52 Flatness parameter, F51, normalized by the size of the QRS amplitude
F53 Flatness evaluated in a asymmetric interval, which on the left side of Tpeak consist of, 80% of the Tstart-TPeak interval, and on the right side 80% of the TPeak-Tend interval
F54 Flatness parameter, F53, normalized by the size of the QRS amplitude
F55 Flatness evaluated in a asymmetric interval, which on the left side of Tpeak consist of, 90% of the Tstart-TPeak interval, and on the right side 90% of the TPeak-Tend interval
F56 Flatness parameter, F55, normalized by the size of the QRS amplitude
F57 Flatness evaluated in a asymmetric interval, which on the left side of Tpeak consist of, 100% of the Tstart-TPeak interval, and on the right side 100% of the TPeak-Tend interval
F58 Flatness parameter, F57, normalized by the size of the QRS amplitude
F59 Flatness evaluated in a asymmetric interval, which on the left side of Center of Mass (CoM) consist of, 10% of the Tstart-TCoM interval, and on the right side 10% of the TCoM-Tend interval
F60 Flatness parameter, F59, normalized by the size of the QRS amplitude
F61 Flatness evaluated in a asymmetric interval, which on the left side of CoM consist of, 20% of the Tstart-TCoM interval, and on the right side 20% of the TCoM-Tend interval
F62 Flatness parameter, F61, normalized by the size of the QRS amplitude
F63 Flatness evaluated in a asymmetric interval, which on the left side of CoM consist of, 30% of the Tstart-TCoM interval, and on the right side 30% of the TCoM-Tend interval
F64 Flatness parameter, F63, normalized by the size of the QRS amplitude
F65 Flatness evaluated in a asymmetric interval, which on the left side of CoM consist of, 40% of the Tstart-TCoM interval, and on the right side 40% of the TCoM-Tend interval
F66 Flatness parameter, F65, normalized by the size of the QRS amplitude
F67 Flatness evaluated in a asymmetric interval, which on the left side of CoM consist of, 50% of the Tstart-TCoM interval, and on the right side 50% of the TCoM-Tend interval
F68 Flatness parameter, F67, normalized by the size of the QRS amplitude
F69 Flatness evaluated in a asymmetric interval, which on the left side of CoM consist of, 60% of the Tstart-TCoM interval, and on the right side 60% of the TCoM-Tend interval
F70 Flatness parameter, F69, normalized by the size of the QRS amplitude
F71 Flatness evaluated in a asymmetric interval, which on the left side of CoM consist of, 70% of the Tstart-TCoM interval, and on the right side 70% of the TCoM-Tend interval
F72 Flatness parameter, F71, normalized by the size of the QRS amplitude
F73 Flatness evaluated in a asymmetric interval, which on the left side of CoM consist of, 80% of the Tstart-TCoM interval, and on the right side 80% of the TCoM-Tend interval
F74 Flatness parameter, F73, normalized by the size of the QRS amplitude
F75 Flatness evaluated in a asymmetric interval, which on the left side of CoM consist of, 90% of the Tstart-TCoM interval, and on the right side 90% of the TCoM-Tend interval
F76 Flatness parameter, F75, normalized by the size of the QRS amplitude
F77 Flatness evaluated in a asymmetric interval, which on the left side of CoM consist of, 100% of the Tstart-TCoM interval, and on the right side 100% of the TCoM-Tend interval
F78 Flatness parameter, F77, normalized by the size of the QRS amplitude
F79 Flatness evaluated in a asymmetric interval, with Tstart at 2% of the area from the j-point to Tend, and Tend at 98% of the area.
F80 Flatness parameter, F79, normalized by the size of the QRS amplitude
F81 Flatness evaluated in a asymmetric interval, with Tstart at 5% of the area from the j-point to Tend, and Tend at 95% of the area.
F82 Flatness parameter, F81, normalized by the size of the QRS amplitude
F83 Flatness evaluated in a asymmetric interval, with Tstart at 2% of the area from the j-point to Tpeak, and Tend at 98% of the area from Tpeak to Tend.
F84 Flatness parameter, F83, normalized by the size of the QRS amplitude
F85 Flatness evaluated in a asymmetric interval, with Tstart at 5% of the area from the j-point to Tpeak, and Tend at 95% of the area from Tpeak to Tend.
F86 Flatness parameter, F85, normalized by the size of the QRS amplitude
F87 Flatness evaluated in a asymmetric interval, with Tstart at 2% of the area from the j-point to CoM, and Tend at 98% of the area from CoM to Tend.
F88 Flatness parameter, F87, normalized by the size of the QRS amplitude
F89 Flatness evaluated in a asymmetric interval, with Tstart at 5% of the area from the j-point to CoM, and Tend at 95% of the area from CoM to Tend.
F90 Flatness parameter, F89, normalized by the size of the QRS amplitude
F91 Peakedness Duration
D1 Variation evaluated in a asymmetric interval, which on the left side of Tpeak consist of, 10% of the Tstart-TPeak interval, and on the right side 10% of the TPeak-Tend interval
D2 Variation evaluated in a asymmetric interval, which on the left side of Tpeak consist of, 20% of the Tstart-TPeak interval, and on the right side 20% of the TPeak-Tend interval
D3 Variation evaluated in a asymmetric interval, which on the left side of Tpeak consist of, 30% of the Tstart-TPeak interval, and on the right side 30% of the TPeak-Tend interval
D4 Variation evaluated in a asymmetric interval, which on the left side of Tpeak consist of, 40% of the Tstart-TPeak interval, and on the right side 40% of the TPeak-Tend interval
D5 Variation evaluated in a asymmetric interval, which on the left side of Tpeak consist of, 50% of the Tstart-TPeak interval, and on the right side 50% of the TPeak-Tend interval D6 Variation evaluated in a asymmetric interval, which on the left side of Tpeak consist of, 60% of the Tstart-TPeak interval, and on the right side 60% of the TPeak-Tend interval D7 Variation evaluated in a asymmetric interval, which on the left side of Tpeak consist of, 70% of the Tstart-TPeak interval, and on the right side 70% of the TPeak-Tend interval D8 Variation evaluated in a asymmetric interval, which on the left side of Tpeak consist of, 80% of the Tstart-TPeak interval, and on the right side 80% of the TPeak-Tend interval D9 Variation evaluated in a asymmetric interval, which on the left side of Tpeak consist of, 90% of the Tstart-TPeak interval, and on the right side 90% of the TPeak-Tend interval D10 Variation evaluated in a asymmetric interval, which on the left side of Tpeak consist of, 100% of the Tstart-TPeak interval, and on the right side 100% of the TPeak-Tend interval D11 Variation evaluated in a asymmetric interval, which on the left side of CoM consist of, 10% of the Tstart-TCoM interval, and on the right side 10% of the TCoM-Tend interval D12 Variation evaluated in a asymmetric interval, which on the left side of CoM consist of, 20% of the Tstart-TCoM interval, and on the right side 20% of the TCoM-Tend interval D13 Variation evaluated in a asymmetric interval, which on the left side of TCoM consist of, 30% of the Tstart-TCoM interval, and on the right side 30% of the TCoM-Tend interval D14 Variation evaluated in a asymmetric interval, which on the left side of CoM consist of, 40% of the Tstart-TCoM interval, and on the right side 40% of the TCoM-Tend interval D15 Variation evaluated in a asymmetric interval, which on the left side of CoM consist of, 50% of the Tstart-TCoM interval, and on the right side 50% of the TCoM-Tend interval D16 Variation evaluated in a asymmetric interval, which on the left side of CoM consist of, 60% of the Tstart-TCoM interval, and on the right side 60% of the TCoM-Tend interval D17 Variation evaluated in a asymmetric interval, which on the left side of CoM consist of, 70% of the Tstart-TCoM interval, and on the right side 70% of the TCoM-Tend interval D18 Variation evaluated in a asymmetric interval, which on the left side of CoM consist of, 80% of the Tstart-TCoM interval, and on the right side 80% of the TCoM-Tend interval D19 Variation evaluated in a asymmetric interval, which on the left side of CoM consist of, 90% of the Tstart-TCoM interval, and on the right side 90% of the TCoM-Tend interval D20 Variation evaluated in a asymmetric interval, which on the left side of CoM consist of, 100% of the Tstart-TCoM interval, and on the right side 100% of the TCoM-Tend interval D21 Variation evaluated in a symmetric interval, 10% of the Tstart-Tend interval, surrounding Tpeak with Tpeak as mean D22 Variation evaluated in a symmetric interval, 20% of the Tstart-Tend interval, surrounding Tpeak with Tpeak as mean D23 Variation evaluated in a symmetric interval, 30% of the Tstart-Tend interval, surrounding Tpeak with Tpeak as mean D24 Variation evaluated in a symmetric interval, 40% of the Tstart-Tend interval, surrounding Tpeak with Tpeak as mean D25 Variation evaluated in a symmetric interval, 50% of the Tstart-Tend interval, surrounding Tpeak with Tpeak as mean D26 Variation evaluated in a symmetric interval, 60% of the Tstart-Tend interval, surrounding Tpeak with Tpeak as mean D27 Variation evaluated in a symmetric interval, 70% of the Tstart-Tend interval, surrounding Tpeak with Tpeak as mean D28 Variation evaluated in a symmetric interval, 80% of the Tstart-Tend interval, surrounding Tpeak with Tpeak as mean D29 Variation evaluated in a symmetric interval, 90% of the Tstart-Tend interval, surrounding Tpeak with Tpeak as mean D30 Variation evaluated in a symmetric interval, 100% of the Tstart-Tend interval, surrounding Tpeak with Tpeak as mean D31 Variation evaluated in a symmetric interval, 10% of the Tstart-Tend interval, surrounding CoM D32 Variation evaluated in a symmetric interval, 20% of the Tstart-Tend interval, surrounding CoM D33 Variation evaluated in a symmetric interval, 30% of the Tstart-Tend interval, surrounding CoM D34 Variation evaluated in a symmetric interval, 40% of the Tstart-Tend interval, surrounding CoM D35 Variation evaluated in a symmetric interval, 50% of the Tstart-Tend interval, surrounding CoM D36 Variation evaluated in a symmetric interval, 60% of the Tstart-Tend interval, surrounding CoM D37 Variation evaluated in a symmetric interval, 70% of the Tstart-Tend interval, surrounding CoM D38 Variation evaluated in a symmetric interval, 80% of the Tstart-Tend interval, surrounding CoM D39 Variation evaluated in a symmetric interval, 90% of the Tstart-Tend interval, surrounding CoM D40 Variation evaluated in a symmetric interval, 100% of the Tstart-Tend interval, surrounding CoM D41 Variation evaluated in a asymmetric interval, with Tstart at 2% of the area from the j-point to Tend, and Tend at 98% of the area.

D42 Variation evaluated in a asymmetric interval, with Tstart at 5% of the area from the j-point to Tend, and Tend at 95% of the area.

D43 Variation evaluated in a asymmetric interval, with Tstart at 2% of the area from the j-point to Tpeak, and Tend at 98% of the area from Tpeak to Tend.

D44 Variation evaluated in a asymmetric interval, with Tstart at 5% of the area from the j-point to Tpeak, and Tend at 95% of the area from Tpeak to Tend.

D45 Variation evaluated in a asymmetric interval, with Tstart at 2% of the area from the j-point to CoM, and Tend at 98% of the area from CoM to Tend.

D46 Variation evaluated in a asymmetric interval, with Tstart at 5% of the area from the j-point to CoM, and Tend at 95% of the area from CoM to Tend.

D47 Duration parameters, D1-D46, normalized by the size of the QRS amplitude

Complexity

C1 Concavity upscore
C2 Concavity parameter, C1, with concavity measure threshold $Thr_{cm}$=0.1
C3 Concavity parameter, C1, with concavity measure threshold $Thr_{cm}$=0.15
C4 Concavity parameter, C1, with concavity measure threshold $Thr_{cm}$=0.2
C5 Concavity parameter, C1, with certainty measure equal to LmRcurv
C6 Concavity parameter, C1, with certainty measure
C7 Concavity parameter, C1, with 30 ms LmRcurv exclusion window, symmetric around Tpeak
C8 Concavity parameter, C1, with 20 ms LmRcurv exclusion window, symmetric around Tpeak
C9 Concavity parameter, C1, with LmRcurv points that correspond in time to ECG amplitude below 20% excluded
C10 Concavity parameter, C1, with LmRcurv points that correspond in time to ECG amplitude below 30% excluded
C11 Concavity parameter, C1, with LmRcurv points that correspond in time to ECG amplitude below 40% excluded
C12 Concavity parameter, C1, with LmRcurv points that correspond in time to ECG amplitude below 50% excluded
C13 Concavity parameter, C1, with LmRcurv points that correspond in time to ECG amplitude below 60% excluded
C14 Concavity parameter, C2 with certainty measure equal to LmRcurv
C15 Concavity parameter, C3, with certainty measure equal to LmRcurv
C16 Concavity parameter, C4, with certainty measure equal to LmRcurv
C17 Concavity parameter, C2 with certainty measure
C18 Concavity parameter, C3, with certainty measure C19 Concavity parameter, C4, with certainty measure
C20 Concavity parameter, C2 with 30 ms LmRcurv exclusion window, symmetric around Tpeak
C21 Concavity parameter, C2 with 20 ms LmRcurv exclusion window, symmetric around Tpeak
C22 Concavity parameter, C3, with 30 ms LmRcurv exclusion window, symmetric around Tpeak
C23 Concavity parameter, C3, with 20 ms LmRcurv exclusion window, symmetric around Tpeak
C24 Concavity parameter, C4, with 30 ms LmRcurv exclusion window, symmetric around Tpeak
C25 Concavity parameter, C4, with 20 ms LmRcurv exclusion window, symmetric around Tpeak
C26 Concavity parameter, C5, with 30 ms LmRcurv exclusion window, symmetric around Tpeak
C27 Concavity parameter, C5, with 20 ms LmRcurv exclusion window, symmetric around Tpeak
C28 Concavity parameter, C6, with 30 ms LmRcurv exclusion window, symmetric around Tpeak
C29 Concavity parameter, C6, with 20 ms LmRcurv exclusion window, symmetric around Tpeak
C30 Concavity parameter, C2 with LmRcurv points that correspond in time to ECG amplitude below 20% excluded
C31 Concavity parameter, C2, with LmRcurv points that correspond in time to ECG amplitude below 30% excluded
C32 Concavity parameter, C2, with LmRcurv points that correspond in time to ECG amplitude below 40% excluded
C33 Concavity parameter, C2, with LmRcurv points that correspond in time to ECG amplitude below 50% excluded
C34 Concavity parameter, C2, with LmRcurv points that correspond in time to ECG amplitude below 60% excluded
C35 Concavity parameter, C3, with LmRcurv points that correspond in time to ECG amplitude below 20% excluded
C36 Concavity parameter, C3, with LmRcurv points that correspond in time to ECG amplitude below 30% excluded
C37 Concavity parameter, C3, with LmRcurv points that correspond in time to ECG amplitude below 40% excluded
C38 Concavity parameter, C3, with LmRcurv points that correspond in time to ECG amplitude below 50% excluded
C39 Concavity parameter, C3, with LmRcurv points that correspond in time to ECG amplitude below 60% excluded
C40 Concavity parameter, C4, with LmRcurv points that correspond in time to ECG amplitude below 20% excluded
C41 Concavity parameter, C4, with LmRcurv points that correspond in time to ECG amplitude below 30% excluded
C42 Concavity parameter, C4, with LmRcurv points that correspond in time to ECG amplitude below 40% excluded
C43 Concavity parameter, C4, with LmRcurv points that correspond in time to ECG amplitude below 50% excluded
C44 Concavity parameter, C4, with LmRcurv points that correspond in time to ECG amplitude below 60% excluded
C45 Concavity parameter, C5, with LmRcurv points that correspond in time to ECG amplitude below 20% excluded
C46 Concavity parameter, C5, with LmRcurv points that correspond in time to ECG amplitude below 30% excluded
C47 Concavity parameter, C5, with LmRcurv points that correspond in time to ECG amplitude below 40% excluded
C48 Concavity parameter, C5, with LmRcurv points that correspond in time to ECG amplitude below 50% excluded
C49 Concavity parameter, C5, with LmRcurv points that correspond in time to ECG amplitude below 60% excluded
C50 Concavity parameter, C6, with LmRcurv points that correspond in time to ECG amplitude below 20% excluded
C51 Concavity parameter, C6, with LmRcurv points that correspond in time to ECG amplitude below 30% excluded
C52 Concavity parameter, C6, with LmRcurv points that correspond in time to ECG amplitude below 40% excluded
C53 Concavity parameter, C6, with LmRcurv points that correspond in time to ECG amplitude below 50% excluded C54 Concavity parameter, C6, with LmRcurv points that correspond in time to ECG amplitude below 60% excluded
C55 Concavity parameter, C7, with LmRcurv points that correspond in time to ECG amplitude below 20% excluded
C56 Concavity parameter, C7, with LmRcurv points that correspond in time to ECG amplitude below 30% excluded
C57 Concavity parameter, C7, with LmRcurv points that correspond in time to ECG amplitude below 40% excluded
C58 Concavity parameter, C7, with LmRcurv points that correspond in time to ECG amplitude below 50% excluded
C59 Concavity parameter, C7, with LmRcurv points that correspond in time to ECG amplitude below 60% excluded
C60 Concavity parameter, C8, with LmRcurv points that correspond in time to ECG amplitude below 20% excluded
C61 Concavity parameter, C8, with LmRcurv points that correspond in time to ECG amplitude below 30% excluded
C62 Concavity parameter, C8, with LmRcurv points that correspond in time to ECG amplitude below 40% excluded
C63 Concavity parameter, C8, with LmRcurv points that correspond in time to ECG amplitude below 50% excluded
C64 Concavity parameter, C8, with LmRcurv points that correspond in time to ECG amplitude below 60% excluded
C65 Concavity parameter, C14, with LmRcurv points that correspond in time to ECG amplitude below 20% excluded
C66 Concavity parameter, C14, with LmRcurv points that correspond in time to ECG amplitude below 30% excluded
C67 Concavity parameter, C14, with LmRcurv points that correspond in time to ECG amplitude below 40% excluded
C68 Concavity parameter, C14, with LmRcurv points that correspond in time to ECG amplitude below 50% excluded
C69 Concavity parameter, C14, with LmRcurv points that correspond in time to ECG amplitude below 60% excluded
C70 Concavity parameter, C15, with LmRcurv points that correspond in time to ECG amplitude below 20% excluded
C71 Concavity parameter, C15, with LmRcurv points that correspond in time to ECG amplitude below 30% excluded
C72 Concavity parameter, C15, with LmRcurv points that correspond in time to ECG amplitude below 40% excluded
C73 Concavity parameter, C15, with LmRcurv points that correspond in time to ECG amplitude below 50% excluded
C74 Concavity parameter, C15, with LmRcurv points that correspond in time to ECG amplitude below 60% excluded
C75 Concavity parameter, C16, with LmRcurv points that correspond in time to ECG amplitude below 20% excluded
C76 Concavity parameter, C16, with LmRcurv points that correspond in time to ECG amplitude below 30% excluded
C77 Concavity parameter, C16, with LmRcurv points that correspond in time to ECG amplitude below 40% excluded
C78 Concavity parameter, C16, with LmRcurv points that correspond in time to ECG amplitude below 50% excluded
C79 Concavity parameter, C16, with LmRcurv points that correspond in time to ECG amplitude below 60% excluded
C80 Concavity parameter, C17, with LmRcurv points that correspond in time to ECG amplitude below 20% excluded
C81 Concavity parameter, C17, with LmRcurv points that correspond in time to ECG amplitude below 30% excluded
C82 Concavity parameter, C17, with LmRcurv points that correspond in time to ECG amplitude below 40% excluded
C83 Concavity parameter, C17, with LmRcurv points that correspond in time to ECG amplitude below 50% excluded
C84 Concavity parameter, C17, with LmRcurv points that correspond in time to ECG amplitude below 60% excluded
C85 Concavity parameter, C18, with LmRcurv points that correspond in time to ECG amplitude below 20% excluded
C86 Concavity parameter, C18, with LmRcurv points that correspond in time to ECG amplitude below 30% excluded
C87 Concavity parameter, C18, with LmRcurv points that correspond in time to ECG amplitude below 40% excluded
C88 Concavity parameter, C18, with LmRcurv points that correspond in time to ECG amplitude below 50% excluded
C89 Concavity parameter, C18, with LmRcurv points that correspond in time to ECG amplitude below 60% excluded
C90 Concavity parameter, C19, with LmRcurv points that correspond in time to ECG amplitude below 20% excluded
C91 Concavity parameter, C19, with LmRcurv points that correspond in time to ECG amplitude below 30% excluded
C92 Concavity parameter, C19, with LmRcurv points that correspond in time to ECG amplitude below 40% excluded
C93 Concavity parameter, C19, with LmRcurv points that correspond in time to ECG amplitude below 50% excluded
C94 Concavity parameter, C19, with LmRcurv points that correspond in time to ECG amplitude below 60% excluded
C95 Concavity parameter, C20, with LmRcurv points that correspond in time to ECG amplitude below 20% excluded
C96 Concavity parameter, C20, with LmRcurv points that correspond in time to ECG amplitude below 30% excluded
C97 Concavity parameter, C20, with LmRcurv points that correspond in time to ECG amplitude below 40% excluded C98 Concavity parameter, C20, with LmRcurv points that correspond in time to ECG amplitude below 50% excluded
C99 Concavity parameter, C20, with LmRcurv points that correspond in time to ECG amplitude below 60% excluded
C100 Concavity parameter, C21, with LmRcurv points that correspond in time to ECG amplitude below 20% excluded
C101 Concavity parameter, C21, with LmRcurv points that correspond in time to ECG amplitude below 30% excluded
C102 Concavity parameter, C21, with LmRcurv points that correspond in time to ECG amplitude below 40% excluded
C103 Concavity parameter, C21, with LmRcurv points that correspond in time to ECG amplitude below 50% excluded
C104 Concavity parameter, C21, with LmRcurv points that correspond in time to ECG amplitude below 60% excluded
C105 Concavity parameter, C22, with LmRcurv points that correspond in time to ECG amplitude below 20% excluded
C106 Concavity parameter, C22, with LmRcurv points that correspond in time to ECG amplitude below 30% excluded
C107 Concavity parameter, C22, with LmRcurv points that correspond in time to ECG amplitude below 40% excluded
C108 Concavity parameter, C22, with LmRcurv points that correspond in time to ECG amplitude below 50% excluded
C109 Concavity parameter, C22, with LmRcurv points that correspond in time to ECG amplitude below 60% excluded
C110 Concavity parameter, C23, with LmRcurv points that correspond in time to ECG amplitude below 20% excluded
C111 Concavity parameter, C23, with LmRcurv points that correspond in time to ECG amplitude below 30% excluded
C112 Concavity parameter, C23, with LmRcurv points that correspond in time to ECG amplitude below 40% excluded
C113 Concavity parameter, C23, with LmRcurv points that correspond in time to ECG amplitude below 50% excluded
C114 Concavity parameter, C23, with LmRcurv points that correspond in time to ECG amplitude below 60% excluded
C115 Concavity parameter, C24, with LmRcurv points that correspond in time to ECG amplitude below 20% excluded
C116 Concavity parameter, C24, with LmRcurv points that correspond in time to ECG amplitude below 30% excluded
C117 Concavity parameter, C24, with LmRcurv points that correspond in time to ECG amplitude below 40% excluded
C118 Concavity parameter, C24, with LmRcurv points that correspond in time to ECG amplitude below 50% excluded
C119 Concavity parameter, C24, with LmRcurv points that correspond in time to ECG amplitude below 60% excluded
C120 Concavity parameter, C25, with LmRcurv points that correspond in time to ECG amplitude below 20% excluded
C121 Concavity parameter, C25, with LmRcurv points that correspond in time to ECG amplitude below 30% excluded
C122 Concavity parameter, C25, with LmRcurv points that correspond in time to ECG amplitude below 40% excluded
C123 Concavity parameter, C25, with LmRcurv points that correspond in time to ECG amplitude below 50% excluded
C124 Concavity parameter, C25, with LmRcurv points that correspond in time to ECG amplitude below 60% excluded
C125 Concavity parameter, C26, with LmRcurv points that correspond in time to ECG amplitude below 20% excluded
C126 Concavity parameter, C26, with LmRcurv points that correspond in time to ECG amplitude below 30% excluded
C127 Concavity parameter, C26, with LmRcurv points that correspond in time to ECG amplitude below 40% excluded
C128 Concavity parameter, C26, with LmRcurv points that correspond in time to ECG amplitude below 50% excluded
C129 Concavity parameter, C26, with LmRcurv points that correspond in time to ECG amplitude below 60% excluded
C130 Concavity parameter, C27, with LmRcurv points that correspond in time to ECG amplitude below 20% excluded
C131 Concavity parameter, C27, with LmRcurv points that correspond in time to ECG amplitude below 30% excluded
C132 Concavity parameter, C27, with LmRcurv points that correspond in time to ECG amplitude below 40% excluded
C133 Concavity parameter, C27, with LmRcurv points that correspond in time to ECG amplitude below 50% excluded
C134 Concavity parameter, C27, with LmRcurv points that correspond in time to ECG amplitude below 60% excluded
C135 Concavity parameter, C28, with LmRcurv points that correspond in time to ECG amplitude below 20% excluded
C136 Concavity parameter, C28, with LmRcurv points that correspond in time to ECG amplitude below 30% excluded
C137 Concavity parameter, C28, with LmRcurv points that correspond in time to ECG amplitude below 40% excluded
C138 Concavity parameter, C28, with LmRcurv points that correspond in time to ECG amplitude below 50% excluded
C139 Concavity parameter, C28, with LmRcurv points that correspond in time to ECG amplitude below 60% excluded
C140 Concavity parameter, C29, with LmRcurv points that correspond in time to ECG amplitude below 20% excluded
C141 Concavity parameter, C29, with LmRcurv points that correspond in time to ECG amplitude below 30% excluded C142 Concavity parameter, C29, with LmRcurv points that correspond in time to ECG amplitude below 40% excluded
C143 Concavity parameter, C29, with LmRcurv points that correspond in time to ECG amplitude below 50% excluded
C144 Concavity parameter, C29, with LmRcurv points that correspond in time to ECG amplitude below 60% excluded
C145 Concavity upscore with CuS=IuS
C146 Concavity parameter, C145, with concavity measure threshold $Thr_{cm}$=0.1
C147 Concavity parameter, C145, with concavity measure threshold $Thr_{cm}$=0.15
C148 Concavity parameter, C145, with concavity measure threshold $Thr_{cm}$=0.2
C149 Concavity parameter, C145, with certainty measure equal to LmRcurv
C150 Concavity parameter, C145, with certainty measure
C151 Concavity parameter, C145, with 30 ms LmRcurv exclusion window, symmetric around Tpeak
C152 Concavity parameter, C145, with 20 ms LmRcurv exclusion window, symmetric around Tpeak
C153 Concavity parameter, C145, with LmRcurv points that correspond in time to ECG amplitude below 20% excluded
C154 Concavity parameter, C145, with LmRcurv points that correspond in time to ECG amplitude below 30% excluded
C155 Concavity parameter, C145, with LmRcurv points that correspond in time to ECG amplitude below 40% excluded
C156 Concavity parameter, C145, with LmRcurv points that correspond in time to ECG amplitude below 50% excluded
C157 Concavity parameter, C145, with LmRcurv points that correspond in time to ECG amplitude below 60% excluded
C158 Concavity parameter, C146, with certainty measure equal to LmRcurv
C159 Concavity parameter, C147, with certainty measure equal to LmRcurv
C160 Concavity parameter, C148, with certainty measure equal to LmRcurv
C161 Concavity parameter, C146, with certainty measure
C162 Concavity parameter, C147, with certainty measure
C163 Concavity parameter, C148, with certainty measure
C164 Concavity parameter, C146, with 30 ms LmRcurv exclusion window, symmetric around Tpeak
C165 Concavity parameter, C146, with 20 ms LmRcurv exclusion window, symmetric around Tpeak
C166 Concavity parameter, C147, with 30 ms LmRcurv exclusion window, symmetric around Tpeak
C167 Concavity parameter, C147, with 20 ms LmRcurv exclusion window, symmetric around Tpeak
C168 Concavity parameter, C148, with 30 ms LmRcurv exclusion window, symmetric around Tpeak
C169 Concavity parameter, C148, with 20 ms LmRcurv exclusion window, symmetric around Tpeak
C170 Concavity parameter, C149, with 30 ms LmRcurv exclusion window, symmetric around Tpeak
C171 Concavity parameter, C149, with 20 ms LmRcurv exclusion window, symmetric around Tpeak
C172 Concavity parameter, C150, with 30 ms LmRcurv exclusion window, symmetric around Tpeak
C173 Concavity parameter, C150, with 20 ms LmRcurv exclusion window, symmetric around Tpeak
C174 Concavity parameter, C146, with LmRcurv points that correspond in time to ECG amplitude below 20% excluded
C175 Concavity parameter, C146, with LmRcurv points that correspond in time to ECG amplitude below 30% excluded
C176 Concavity parameter, C146, with LmRcurv points that correspond in time to ECG amplitude below 40% excluded
C177 Concavity parameter, C146, with LmRcurv points that correspond in time to ECG amplitude below 50% excluded
C178 Concavity parameter, C146, with LmRcurv points that correspond in time to ECG amplitude below 60% excluded
C179 Concavity parameter, C147, with LmRcurv points that correspond in time to ECG amplitude below 20% excluded
C180 Concavity parameter, C147, with LmRcurv points that correspond in time to ECG amplitude below 30% excluded
C181 Concavity parameter, C147, with LmRcurv points that correspond in time to ECG amplitude below 40% excluded
C182 Concavity parameter, C147, with LmRcurv points that correspond in time to ECG amplitude below 50% excluded
C183 Concavity parameter, C147, with LmRcurv points that correspond in time to ECG amplitude below 60% excluded
C184 Concavity parameter, C148, with LmRcurv points that correspond in time to ECG amplitude below 20% excluded
C185 Concavity parameter, C148, with LmRcurv points that correspond in time to ECG amplitude below 30% excluded
C186 Concavity parameter, C148, with LmRcurv points that correspond in time to ECG amplitude below 40% excluded
C187 Concavity parameter, C148, with LmRcurv points that correspond in time to ECG amplitude below 50% excluded
C188 Concavity parameter, C148, with LmRcurv points that correspond in time to ECG amplitude below 60% excluded
C189 Concavity parameter, C149, with LmRcurv points that correspond in time to ECG amplitude below 20% excluded
C190 Concavity parameter, C149, with LmRcurv points that correspond in time to ECG amplitude below 30% excluded
C191 Concavity parameter, C149, with LmRcurv points that correspond in time to ECG amplitude below 40% excluded
C192 Concavity parameter, C149, with LmRcurv points that correspond in time to ECG amplitude below 50% excluded
C193 Concavity parameter, C149, with LmRcurv points that correspond in time to ECG amplitude below 60% excluded
C194 Concavity parameter, C150, with LmRcurv points that correspond in time to ECG amplitude below 20% excluded
C195 Concavity parameter, C150, with LmRcurv points that correspond in time to ECG amplitude below 30% excluded C196 Concavity parameter, C150, with LmRcurv points that correspond in time to ECG amplitude below 40% excluded
C197 Concavity parameter, C150, with LmRcurv points that correspond in time to ECG amplitude below 50% excluded
C198 Concavity parameter, C150, with LmRcurv points that correspond in time to ECG amplitude below 60% excluded
C199 Concavity parameter, C151, with LmRcurv points that correspond in time to ECG amplitude below 20% excluded
C200 Concavity parameter, C151, with LmRcurv points that correspond in time to ECG amplitude below 30% excluded
C201 Concavity parameter, C151, with LmRcurv points that correspond in time to ECG amplitude below 40% excluded
C202 Concavity parameter, C151, with LmRcurv points that correspond in time to ECG amplitude below 50% excluded
C203 Concavity parameter, C151, with LmRcurv points that correspond in time to ECG amplitude below 60% excluded
C204 Concavity parameter, C152, with LmRcurv points that correspond in time to ECG amplitude below 20% excluded
C205 Concavity parameter, C152, with LmRcurv points that correspond in time to ECG amplitude below 30% excluded
C206 Concavity parameter, C152, with LmRcurv points that correspond in time to ECG amplitude below 40% excluded
C207 Concavity parameter, C152, with LmRcurv points that correspond in time to ECG amplitude below 50% excluded
C208 Concavity parameter, C152, with LmRcurv points that correspond in time to ECG amplitude below 60% excluded
C209 Concavity parameter, C158, with LmRcurv points that correspond in time to ECG amplitude below 20% excluded
C210 Concavity parameter, C158, with LmRcurv points that correspond in time to ECG amplitude below 30% excluded
C211 Concavity parameter, C158, with LmRcurv points that correspond in time to ECG amplitude below 40% excluded
C212 Concavity parameter, C158, with LmRcurv points that correspond in time to ECG amplitude below 50% excluded
C213 Concavity parameter, C158, with LmRcurv points that correspond in time to ECG amplitude below 60% excluded
C214 Concavity parameter, C159, with LmRcurv points that correspond in time to ECG amplitude below 20% excluded
C215 Concavity parameter, C159, with LmRcurv points that correspond in time to ECG amplitude below 30% excluded
C216 Concavity parameter, C159, with LmRcurv points that correspond in time to ECG amplitude below 40% excluded
C217 Concavity parameter, C159, with LmRcurv points that correspond in time to ECG amplitude below 50% excluded
C218 Concavity parameter, C159, with LmRcurv points that correspond in time to ECG amplitude below 60% excluded
C219 Concavity parameter, C160, with LmRcurv points that correspond in time to ECG amplitude below 20% excluded
C220 Concavity parameter, C160, with LmRcurv points that correspond in time to ECG amplitude below 30% excluded
C221 Concavity parameter, C160, with LmRcurv points that correspond in time to ECG amplitude below 40% excluded
C222 Concavity parameter, C160, with LmRcurv points that correspond in time to ECG amplitude below 50% excluded
C223 Concavity parameter, C160, with LmRcurv points that correspond in time to ECG amplitude below 60% excluded
C224 Concavity parameter, C161, with LmRcurv points that correspond in time to ECG amplitude below 20% excluded
C225 Concavity parameter, C161, with LmRcurv points that correspond in time to ECG amplitude below 30% excluded
C226 Concavity parameter, C161, with LmRcurv points that correspond in time to ECG amplitude below 40% excluded
C227 Concavity parameter, C161, with LmRcurv points that correspond in time to ECG amplitude below 50% excluded
C228 Concavity parameter, C161, with LmRcurv points that correspond in time to ECG amplitude below 60% excluded
C229 Concavity parameter, C162, with LmRcurv points that correspond in time to ECG amplitude below 20% excluded
C230 Concavity parameter, C162, with LmRcurv points that correspond in time to ECG amplitude below 30% excluded
C231 Concavity parameter, C162, with LmRcurv points that correspond in time to ECG amplitude below 40% excluded
C232 Concavity parameter, C162, with LmRcurv points that correspond in time to ECG amplitude below 50% excluded
C233 Concavity parameter, C162, with LmRcurv points that correspond in time to ECG amplitude below 60% excluded
C234 Concavity parameter, C163, with LmRcurv points that correspond in time to ECG amplitude below 20% excluded
C235 Concavity parameter, C163, with LmRcurv points that correspond in time to ECG amplitude below 30% excluded
C236 Concavity parameter, C163, with LmRcurv points that correspond in time to ECG amplitude below 40% excluded
C237 Concavity parameter, C163, with LmRcurv points that correspond in time to ECG amplitude below 50% excluded
C238 Concavity parameter, C163 with LmRcurv points that correspond in time to ECG amplitude below 60% excluded
C239 Concavity parameter, C164, with LmRcurv points that correspond in time to ECG amplitude below 20% excluded C240 Concavity parameter, C164, with LmRcurv points that correspond in time to ECG amplitude below 30% excluded
C241 Concavity parameter, C164, with LmRcurv points that correspond in time to ECG amplitude below 40% excluded
C242 Concavity parameter, C164, with LmRcurv points that correspond in time to ECG amplitude below 50% excluded
C243 Concavity parameter, C164, with LmRcurv points that correspond in time to ECG amplitude below 60% excluded
C244 Concavity parameter, C165, with LmRcurv points that correspond in time to ECG amplitude below 20% excluded
C245 Concavity parameter, C165, with LmRcurv points that correspond in time to ECG amplitude below 30% excluded
C246 Concavity parameter, C165, with LmRcurv points that correspond in time to ECG amplitude below 40% excluded
C247 Concavity parameter, C165, with LmRcurv points that correspond in time to ECG amplitude below 50% excluded
C248 Concavity parameter, C165, with LmRcurv points that correspond in time to ECG amplitude below 60% excluded
C249 Concavity parameter, C166, with LmRcurv points that correspond in time to ECG amplitude below 20% excluded
C250 Concavity parameter, C166, with LmRcurv points that correspond in time to ECG amplitude below 30% excluded
C251 Concavity parameter, C166, with LmRcurv points that correspond in time to ECG amplitude below 40% excluded
C252 Concavity parameter, C166, with LmRcurv points that correspond in time to ECG amplitude below 50% excluded
C253 Concavity parameter, C166, with LmRcurv points that correspond in time to ECG amplitude below 60% excluded
C254 Concavity parameter, C167, with LmRcurv points that correspond in time to ECG amplitude below 20% excluded
C255 Concavity parameter, C167, with LmRcurv points that correspond in time to ECG amplitude below 30% excluded
C256 Concavity parameter, C167, with LmRcurv points that correspond in time to ECG amplitude below 40% excluded
C257 Concavity parameter, C167, with LmRcurv points that correspond in time to ECG amplitude below 50% excluded
C258 Concavity parameter, C167, with LmRcurv points that correspond in time to ECG amplitude below 60% excluded
C259 Concavity parameter, C168, with LmRcurv points that correspond in time to ECG amplitude below 20% excluded
C260 Concavity parameter, C168, with LmRcurv points that correspond in time to ECG amplitude below 30% excluded
C261 Concavity parameter, C168, with LmRcurv points that correspond in time to ECG amplitude below 40% excluded
C262 Concavity parameter, C168, with LmRcurv points that correspond in time to ECG amplitude below 50% excluded
C263 Concavity parameter, C168, with LmRcurv points that correspond in time to ECG amplitude below 60% excluded
C264 Concavity parameter, C169, with LmRcurv points that correspond in time to ECG amplitude below 20% excluded
C265 Concavity parameter, C169, with LmRcurv points that correspond in time to ECG amplitude below 30% excluded
C266 Concavity parameter, C169, with LmRcurv points that correspond in time to ECG amplitude below 40% excluded
C267 Concavity parameter, C169, with LmRcurv points that correspond in time to ECG amplitude below 50% excluded
C268 Concavity parameter, C169, with LmRcurv points that correspond in time to ECG amplitude below 60% excluded
C269 Concavity parameter, C170, with LmRcurv points that correspond in time to ECG amplitude below 20% excluded
C270 Concavity parameter, C170, with LmRcurv points that correspond in time to ECG amplitude below 30% excluded
C271 Concavity parameter, C170, with LmRcurv points that correspond in time to ECG amplitude below 40% excluded
C272 Concavity parameter, C170, with LmRcurv points that correspond in time to ECG amplitude below 50% excluded
C273 Concavity parameter, C170, with LmRcurv points that correspond in time to ECG amplitude below 60% excluded
C274 Concavity parameter, C171, with LmRcurv points that correspond in time to ECG amplitude below 20% excluded
C275 Concavity parameter, C171, with LmRcurv points that correspond in time to ECG amplitude below 30% excluded
C276 Concavity parameter, C171, with LmRcurv points that correspond in time to ECG amplitude below 40% excluded
C277 Concavity parameter, C171, with LmRcurv points that correspond in time to ECG amplitude below 50% excluded
C278 Concavity parameter, C171, with LmRcurv points that correspond in time to ECG amplitude below 60% excluded
C279 Concavity parameter, C172, with LmRcurv points that correspond in time to ECG amplitude below 20% excluded
C280 Concavity parameter, C172, with LmRcurv points that correspond in time to ECG amplitude below 30% excluded
C281 Concavity parameter, C172, with LmRcurv points that correspond in time to ECG amplitude below 40% excluded
C282 Concavity parameter, C172, with LmRcurv points that correspond in time to ECG amplitude below 50% excluded
C283 Concavity parameter, C172, with LmRcurv points that correspond in time to ECG amplitude below 60% excluded C284 Concavity parameter, C173, with LmRcurv points that correspond in time to ECG amplitude below 20% excluded
C285 Concavity parameter, C173, with LmRcurv points that correspond in time to ECG amplitude below 30% excluded
C286 Concavity parameter, C173, with LmRcurv points that correspond in time to ECG amplitude below 40% excluded
C287 Concavity parameter, C173, with LmRcurv points that correspond in time to ECG amplitude below 50% excluded
C288 Concavity parameter, C173, with LmRcurv points that correspond in time to ECG amplitude below 60% excluded
C289 Concavity downscore
C290 Concavity parameter, C289, with concavity measure threshold $Thr_{cm}=0.1$
C291 Concavity parameter, C289, with concavity measure threshold $Thr_{cm}=0.15$
C292 Concavity parameter, C289, with concavity measure threshold $Thr_{cm}=0.2$
C293 Concavity parameter, C289, with certainty measure equal to LmRcurv
C294 Concavity parameter, C289, with certainty measure
C295 Concavity parameter, C289, with 30 ms LmRcurv exclusion window, symmetric around Tpeak
C296 Concavity parameter, C289, with 20 ms LmRcurv exclusion window, symmetric around Tpeak
C297 Concavity parameter, C289, with LmRcurv points that correspond in time to ECG amplitude below 20% excluded
C298 Concavity parameter, C289, with LmRcurv points that correspond in time to ECG amplitude below 30% excluded
C299 Concavity parameter, C289, with LmRcurv points that correspond in time to ECG amplitude below 40% excluded
C300 Concavity parameter, C289, with LmRcurv points that correspond in time to ECG amplitude below 50% excluded
C301 Concavity parameter, C289, with LmRcurv points that correspond in time to ECG amplitude below 60% excluded
C302 Concavity parameter, C290, with certainty measure equal to LmRcurv
C303 Concavity parameter, C291, with certainty measure equal to LmRcurv
C304 Concavity parameter, C292, with certainty measure equal to LmRcurv
C305 Concavity parameter, C290, with certainty measure
C306 Concavity parameter, C291, with certainty measure
C307 Concavity parameter, C292, with certainty measure
C308 Concavity parameter, C290, with 30 ms LmRcurv exclusion window, symmetric around Tpeak
C309 Concavity parameter, C290, with 20 ms LmRcurv exclusion window, symmetric around Tpeak
C310 Concavity parameter, C291, with 30 ms LmRcurv exclusion window, symmetric around Tpeak
C311 Concavity parameter, C291, with 20 ms LmRcurv exclusion window, symmetric around Tpeak
C312 Concavity parameter, C292, with 30 ms LmRcurv exclusion window, symmetric around Tpeak
C313 Concavity parameter, C292, with 20 ms LmRcurv exclusion window, symmetric around Tpeak
C314 Concavity parameter, C293, with 30 ms LmRcurv exclusion window, symmetric around Tpeak
C315 Concavity parameter, C293, with 20 ms LmRcurv exclusion window, symmetric around Tpeak
C316 Concavity parameter, C294, with 30 ms LmRcurv exclusion window, symmetric around Tpeak
C317 Concavity parameter, C294, with 20 ms LmRcurv exclusion window, symmetric around Tpeak
C318 Concavity parameter, C290 with LmRcurv points that correspond in time to ECG amplitude below 20% excluded
C319 Concavity parameter, C290 with LmRcurv points that correspond in time to ECG amplitude below 30% excluded
C320 Concavity parameter, C290 with LmRcurv points that correspond in time to ECG amplitude below 40% excluded
C321 Concavity parameter, C290 with LmRcurv points that correspond in time to ECG amplitude below 50% excluded
C322 Concavity parameter, C290 with LmRcurv points that correspond in time to ECG amplitude below 60% excluded
C323 Concavity parameter, C291, with LmRcurv points that correspond in time to ECG amplitude below 20% excluded
C324 Concavity parameter, C291, with LmRcurv points that correspond in time to ECG amplitude below 30% excluded
C325 Concavity parameter, C291, with LmRcurv points that correspond in time to ECG amplitude below 40% excluded
C326 Concavity parameter, C291, with LmRcurv points that correspond in time to ECG amplitude below 50% excluded
C327 Concavity parameter, C291, with LmRcurv points that correspond in time to ECG amplitude below 60% excluded
C328 Concavity parameter, C292, with LmRcurv points that correspond in time to ECG amplitude below 20% excluded
C329 Concavity parameter, C292, with LmRcurv points that correspond in time to ECG amplitude below 30% excluded
C330 Concavity parameter, C292, with LmRcurv points that correspond in time to ECG amplitude below 40% excluded
C331 Concavity parameter, C292, with LmRcurv points that correspond in time to ECG amplitude below 50% excluded
C332 Concavity parameter, C292, with LmRcurv points that correspond in time to ECG amplitude below 60% excluded
C333 Concavity parameter, C293, with LmRcurv points that correspond in time to ECG amplitude below 20% excluded
C334 Concavity parameter, C293, with LmRcurv points that correspond in time to ECG amplitude below 30% excluded
C335 Concavity parameter, C293, with LmRcurv points that correspond in time to ECG amplitude below 40% excluded
C336 Concavity parameter, C293, with LmRcurv points that correspond in time to ECG amplitude below 50% excluded
C337 Concavity parameter, C293, with LmRcurv points that correspond in time to ECG amplitude below 60% excluded C338 Concavity parameter, C294, with LmRcurv points that correspond in time to ECG amplitude below 20% excluded
C339 Concavity parameter, C294, with LmRcurv points that correspond in time to ECG amplitude below 30% excluded
C340 Concavity parameter, C294, with LmRcurv points that correspond in time to ECG amplitude below 40% excluded
C341 Concavity parameter, C294, with LmRcurv points that correspond in time to ECG amplitude below 50% excluded
C342 Concavity parameter, C294, with LmRcurv points that correspond in time to ECG amplitude below 60% excluded
C343 Concavity parameter, C295, with LmRcurv points that correspond in time to ECG amplitude below 20% excluded
C344 Concavity parameter, C295, with LmRcurv points that correspond in time to ECG amplitude below 30% excluded
C345 Concavity parameter, C295, with LmRcurv points that correspond in time to ECG amplitude below 40% excluded
C346 Concavity parameter, C295, with LmRcurv points that correspond in time to ECG amplitude below 50% excluded
C347 Concavity parameter, C295, with LmRcurv points that correspond in time to ECG amplitude below 60% excluded
C348 Concavity parameter, C296, with LmRcurv points that correspond in time to ECG amplitude below 20% excluded
C349 Concavity parameter, C296, with LmRcurv points that correspond in time to ECG amplitude below 30% excluded
C350 Concavity parameter, C296, with LmRcurv points that correspond in time to ECG amplitude below 40% excluded
C351 Concavity parameter, C296, with LmRcurv points that correspond in time to ECG amplitude below 50% excluded
C352 Concavity parameter, C296, with LmRcurv points that correspond in time to ECG amplitude below 60% excluded
C353 Concavity parameter, C302, with LmRcurv points that correspond in time to ECG amplitude below 20% excluded
C354 Concavity parameter, C302, with LmRcurv points that correspond in time to ECG amplitude below 30% excluded
C355 Concavity parameter, C302, with LmRcurv points that correspond in time to ECG amplitude below 40% excluded
C356 Concavity parameter, C302, with LmRcurv points that correspond in time to ECG amplitude below 50% excluded
C357 Concavity parameter, C302, with LmRcurv points that correspond in time to ECG amplitude below 60% excluded
C358 Concavity parameter, C303, with LmRcurv points that correspond in time to ECG amplitude below 20% excluded
C359 Concavity parameter, C303, with LmRcurv points that correspond in time to ECG amplitude below 30% excluded
C360 Concavity parameter, C303, with LmRcurv points that correspond in time to ECG amplitude below 40% excluded
C361 Concavity parameter, C303, with LmRcurv points that correspond in time to ECG amplitude below 50% excluded
C362 Concavity parameter, C303, with LmRcurv points that correspond in time to ECG amplitude below 60% excluded
C363 Concavity parameter, C304, with LmRcurv points that correspond in time to ECG amplitude below 20% excluded
C364 Concavity parameter, C304, with LmRcurv points that correspond in time to ECG amplitude below 30% excluded
C365 Concavity parameter, C304, with LmRcurv points that correspond in time to ECG amplitude below 40% excluded
C366 Concavity parameter, C304, with LmRcurv points that correspond in time to ECG amplitude below 50% excluded
C367 Concavity parameter, C304, with LmRcurv points that correspond in time to ECG amplitude below 60% excluded
C368 Concavity parameter, C305, with LmRcurv points that correspond in time to ECG amplitude below 20% excluded
C369 Concavity parameter, C305, with LmRcurv points that correspond in time to ECG amplitude below 30% excluded
C370 Concavity parameter, C305, with LmRcurv points that correspond in time to ECG amplitude below 40% excluded
C371 Concavity parameter, C305, with LmRcurv points that correspond in time to ECG amplitude below 50% excluded
C372 Concavity parameter, C305, with LmRcurv points that correspond in time to ECG amplitude below 60% excluded
C373 Concavity parameter, C306, with LmRcurv points that correspond in time to ECG amplitude below 20% excluded
C374 Concavity parameter, C306, with LmRcurv points that correspond in time to ECG amplitude below 30% excluded
C375 Concavity parameter, C306, with LmRcurv points that correspond in time to ECG amplitude below 40% excluded
C376 Concavity parameter, C306, with LmRcurv points that correspond in time to ECG amplitude below 50% excluded
C377 Concavity parameter, C306, with LmRcurv points that correspond in time to ECG amplitude below 60% excluded
C378 Concavity parameter, C307, with LmRcurv points that correspond in time to ECG amplitude below 20% excluded
C379 Concavity parameter, C307, with LmRcurv points that correspond in time to ECG amplitude below 30% excluded
C380 Concavity parameter, C307, with LmRcurv points that correspond in time to ECG amplitude below 40% excluded
C381 Concavity parameter, C307, with LmRcurv points that correspond in time to ECG amplitude below 50% excluded C382 Concavity parameter, C307, with LmRcurv points that correspond in time to ECG amplitude below 60% excluded
C383 Concavity parameter, C308, with LmRcurv points that correspond in time to ECG amplitude below 20% excluded
C384 Concavity parameter, C308, with LmRcurv points that correspond in time to ECG amplitude below 30% excluded
C385 Concavity parameter, C308, with LmRcurv points that correspond in time to ECG amplitude below 40% excluded
C386 Concavity parameter, C308, with LmRcurv points that correspond in time to ECG amplitude below 50% excluded
C387 Concavity parameter, C308, with LmRcurv points that correspond in time to ECG amplitude below 60% excluded
C388 Concavity parameter, C309, with LmRcurv points that correspond in time to ECG amplitude below 20% excluded
C389 Concavity parameter, C309, with LmRcurv points that correspond in time to ECG amplitude below 30% excluded
C390 Concavity parameter, C309, with LmRcurv points that correspond in time to ECG amplitude below 40% excluded
C391 Concavity parameter, C309, with LmRcurv points that correspond in time to ECG amplitude below 50% excluded
C392 Concavity parameter, C309, with LmRcurv points that correspond in time to ECG amplitude below 60% excluded
C393 Concavity parameter, C310, with LmRcurv points that correspond in time to ECG amplitude below 20% excluded
C394 Concavity parameter, C310, with LmRcurv points that correspond in time to ECG amplitude below 30% excluded
C395 Concavity parameter, C310, with LmRcurv points that correspond in time to ECG amplitude below 40% excluded
C396 Concavity parameter, C310, with LmRcurv points that correspond in time to ECG amplitude below 50% excluded
C397 Concavity parameter, C310, with LmRcurv points that correspond in time to ECG amplitude below 60% excluded
C398 Concavity parameter, C311, with LmRcurv points that correspond in time to ECG amplitude below 20% excluded
C399 Concavity parameter, C311, with LmRcurv points that correspond in time to ECG amplitude below 30% excluded
C400 Concavity parameter, C311, with LmRcurv points that correspond in time to ECG amplitude below 40% excluded
C401 Concavity parameter, C311, with LmRcurv points that correspond in time to ECG amplitude below 50% excluded
C402 Concavity parameter, C311, with LmRcurv points that correspond in time to ECG amplitude below 60% excluded
C403 Concavity parameter, C312, with LmRcurv points that correspond in time to ECG amplitude below 20% excluded
C404 Concavity parameter, C312, with LmRcurv points that correspond in time to ECG amplitude below 30% excluded
C405 Concavity parameter, C312, with LmRcurv points that correspond in time to ECG amplitude below 40% excluded
C406 Concavity parameter, C312, with LmRcurv points that correspond in time to ECG amplitude below 50% excluded
C407 Concavity parameter, C312, with LmRcurv points that correspond in time to ECG amplitude below 60% excluded
C408 Concavity parameter, C313, with LmRcurv points that correspond in time to ECG amplitude below 20% excluded
C409 Concavity parameter, C313, with LmRcurv points that correspond in time to ECG amplitude below 30% excluded
C410 Concavity parameter, C313, with LmRcurv points that correspond in time to ECG amplitude below 40% excluded
C411 Concavity parameter, C313, with LmRcurv points that correspond in time to ECG amplitude below 50% excluded
C412 Concavity parameter, C313, with LmRcurv points that correspond in time to ECG amplitude below 60% excluded
C413 Concavity parameter, C314, with LmRcurv points that correspond in time to ECG amplitude below 20% excluded
C414 Concavity parameter, C314, with LmRcurv points that correspond in time to ECG amplitude below 30% excluded
C415 Concavity parameter, C314, with LmRcurv points that correspond in time to ECG amplitude below 40% excluded
C416 Concavity parameter, C314 with LmRcurv points that correspond in time to ECG amplitude below 50% excluded
C417 Concavity parameter, C314, with LmRcurv points that correspond in time to ECG amplitude below 60% excluded
C418 Concavity parameter, C315, with LmRcurv points that correspond in time to ECG amplitude below 20% excluded
C419 Concavity parameter, C315, with LmRcurv points that correspond in time to ECG amplitude below 30% excluded
C420 Concavity parameter, C315, with LmRcurv points that correspond in time to ECG amplitude below 40% excluded
C421 Concavity parameter, C315, with LmRcurv points that correspond in time to ECG amplitude below 50% excluded
C422 Concavity parameter, C315, with LmRcurv points that correspond in time to ECG amplitude below 60% excluded
C423 Concavity parameter, C316, with LmRcurv points that correspond in time to ECG amplitude below 20% excluded
C424 Concavity parameter, C316, with LmRcurv points that correspond in time to ECG amplitude below 30% excluded
C425 Concavity parameter, C316, with LmRcurv points that correspond in time to ECG amplitude below 40% excluded C426 Concavity parameter, C316, with LmRcurv points that correspond in time to ECG amplitude below 50% excluded
C427 Concavity parameter, C316, with LmRcurv points that correspond in time to ECG amplitude below 60% excluded
C428 Concavity parameter, C317, with LmRcurv points that correspond in time to ECG amplitude below 20% excluded
C429 Concavity parameter, C317, with LmRcurv points that correspond in time to ECG amplitude below 30% excluded
C430 Concavity parameter, C317, with LmRcurv points that correspond in time to ECG amplitude below 40% excluded
C431 Concavity parameter, C317, with LmRcurv points that correspond in time to ECG amplitude below 50% excluded
C432 Concavity parameter, C317, with LmRcurv points that correspond in time to ECG amplitude below 60% excluded
C433 Concavity parameter, C17 with 20 ms LmRcurv exclusion window, symmetric around Tpeak
C434 Concavity parameter, C18 with 20 ms LmRcurv exclusion window, symmetric around Tpeak
C435 Concavity parameter, C19 with 20 ms LmRcurv exclusion window, symmetric around Tpeak
C436 Concavity parameter, C433, with LmRcurv points that correspond in time to ECG amplitude below 20% excluded
C437 Concavity parameter, C433, with LmRcurv points that correspond in time to ECG amplitude below 30% excluded
C438 Concavity parameter, C433, with LmRcurv points that correspond in time to ECG amplitude below 40% excluded
C439 Concavity parameter, C433, with LmRcurv points that correspond in time to ECG amplitude below 50% excluded
C440 Concavity parameter, C433, with LmRcurv points that correspond in time to ECG amplitude below 60% excluded
C441 Concavity parameter, C434, with LmRcurv points that correspond in time to ECG amplitude below 20% excluded
C442 Concavity parameter, C434, with LmRcurv points that correspond in time to ECG amplitude below 30% excluded
C443 Concavity parameter, C434, with LmRcurv points that correspond in time to ECG amplitude below 40% excluded
C444 Concavity parameter, C434, with LmRcurv points that correspond in time to ECG amplitude below 50% excluded
C445 Concavity parameter, C434, with LmRcurv points that correspond in time to ECG amplitude below 60% excluded
C446 Concavity parameter, C435, with LmRcurv points that correspond in time to ECG amplitude below 20% excluded
C447 Concavity parameter, C435, with LmRcurv points that correspond in time to ECG amplitude below 30% excluded
C448 Concavity parameter, C435, with LmRcurv points that correspond in time to ECG amplitude below 40% excluded
C449 Concavity parameter, C435, with LmRcurv points that correspond in time to ECG amplitude below 50% excluded
C450 Concavity parameter, C435, with LmRcurv points that correspond in time to ECG amplitude below 60% excluded
C451 Concavity parameter, C161, with 20 ms LmRcurv exclusion window, symmetric around Tpeak
C452 Concavity parameter, C162, with 20 ms LmRcurv exclusion window, symmetric around Tpeak
C453 Concavity parameter, C163, with 20 ms LmRcurv exclusion window, symmetric around Tpeak
C454 Concavity parameter, C451, with LmRcurv points that correspond in time to ECG amplitude below 20% excluded
C455 Concavity parameter, C451, with LmRcurv points that correspond in time to ECG amplitude below 30% excluded
C456 Concavity parameter, C451, with LmRcurv points that correspond in time to ECG amplitude below 40% excluded
C457 Concavity parameter, C451, with LmRcurv points that correspond in time to ECG amplitude below 50% excluded
C458 Concavity parameter, C451, with LmRcurv points that correspond in time to ECG amplitude below 60% excluded
C459 Concavity parameter, C452, with LmRcurv points that correspond in time to ECG amplitude below 20% excluded
C460 Concavity parameter, C452, with LmRcurv points that correspond in time to ECG amplitude below 30% excluded
C461 Concavity parameter, C452, with LmRcurv points that correspond in time to ECG amplitude below 40% excluded
C462 Concavity parameter, C452, with LmRcurv points that correspond in time to ECG amplitude below 50% excluded
C463 Concavity parameter, C452, with LmRcurv points that correspond in time to ECG amplitude below 60% excluded
C464 Concavity parameter, C453, with LmRcurv points that correspond in time to ECG amplitude below 20% excluded
C465 Concavity parameter, C453, with LmRcurv points that correspond in time to ECG amplitude below 30% excluded
C466 Concavity parameter, C453, with LmRcurv points that correspond in time to ECG amplitude below 40% excluded
C467 Concavity parameter, C453, with LmRcurv points that correspond in time to ECG amplitude below 50% excluded
C468 Concavity parameter, C453, with LmRcurv points that correspond in time to ECG amplitude below 60% excluded

The invention claimed is:
1. System for analysis of ECG curvature comprising a computer system, which computer system performs a mathematical analysis, which mathematical analysis comprises at least the following steps:
   a: the system comprises input means connected to at least one ECG source,
   b: a number of different parameters are isolated and stored in the computer system, c: the computer system select a first number of parameters from at least one main group, d: the computer system combine the selected parameters in at least a first mathematical analysis, whereby the parameters are selected from groups of symmetry (S1-S72), flatness (F1-F91), duration (D1-D47) and/or complexity (C1-C468), e: extract a segment in of the ECG curvature in the mathematical analysis, f: which segment is corresponding to a interval between defined electrocardiographic points, g: which segment is used as input to a first algorithm, h: where a second fiducial point algorithm automatically calculates fiducial points at the segment, i: where concavity intervals are evaluated on subsegments of the ECG segment and form the basis of up- and downwards concavity quantification, j: where the system based on at least the first and the second algorithm detects and quantifies concavity on ECG curvatures;

wherein at least one segment of the ECG repolarization signal is selected, corresponding to the interval between the Twave onset and Twave offset, which segment is normalized so that the amplitude range (y) is equal to a first predefined value in the selected interval.

2. A system according to claim 1, wherein at least one segment of the ECG repolarization signal is selected, corresponding to the interval between the Twave onset and Twave offset, which segment is normalized so that the duration (x) is equal to a second predefined value in the selected interval.

3. A system according to one of the claim 2, wherein the first and second derivatives (with respect to time) of the ECG repolarization segment are determined on the interval between the Twave onset and Twave offset, where the two derivative signals are subsequently used to calculate a radius of curvature (Rcurv) signal using the equation 1:

$$Rcurv = -\frac{\left[1+\left(\frac{dy}{dx}\right)^2\right]^{3/2}}{\frac{d^2y}{dx^2}} \qquad \text{Equation 1}$$

where x is the timescale and y is the (ECG) signal.

4. A system according to claim 3, wherein local maxima (LmRcurv) on the Rcurv signal between any two repolarization fiducial points is determined to identify places of local downwards concavity on a repolarization segment of an ECG.

5. A system according to claim 4, wherein local minima on the Rcurv signal between any two repolarization fiducial points are determined to identify places of local upwards concavity on a repolarization segment of an ECG.

6. A system according to claim 5, wherein the Rcurv signal is investigated further to identify any contiguous configuration of local maximum neighbored by local minimum on the Rcury signal, where the values of the identified maximum and minimum are used to evaluate the size of any concavity on a repolarization segment of an ECG.

7. A system according to claim 3, wherein a window is defined in a curve segment stating at a first defined period before Twave peak and ending at a second defined period after Twave peak, in which window the curvature is excluded from further analysis of the Rcurv signal, and where any number of LmRcurv signal values with amplitudes below zero is excluded from further analysis, where any number of LmRcurv signal values, which correspond in time to ECG repolarization amplitudes below any given threshold are excluded from further analysis.

8. A system according to claim 3, wherein positive segment durations on the Rcurv on either side of all reference points are multiplied by the value of the corresponding LmRcurv values to obtain certainty measures (Cm) of the presence of local downward concavities.

9. A system according to claim 8, wherein certainty measures exceeding a threshold (Thr) are defined as places around which concavity intervals are defined and local downward concavities are quantified.

10. A system according to claim 9, wherein no certainty measures exceeding a threshold (Thr) are present, where a first subsegment is generated by two piecewise tilted segments, where a first tilted subsegment ($T_{1tilt}$) is given by the repolarization interval between the Twave onset and Twave peak from which the linear function between the two endpoints is subtracted, where a second tilted subsegment ($T_{2tilt}$) is given by the repolarization interval between the Twave peak and Twave offset from which the linear function between the two endpoints is subtracted.

11. A system according to claim 10, wherein an upwards concavity score is calculated, where the least negative minimum on either piecewise repolarization subsegment is used as an initial upwards concavity score (IuS), which score is corrected to obtain a final upwards concavity score (CuS), where the relationship is given by equation 3:

$$CuS = IuS\left(1 - \frac{Cm}{Thr}\right). \qquad \text{Equation 3}$$

12. A system according to claim 9, wherein certainty measures exceeding a threshold (Thr) are present, where at least one third subsegment is generated by piecewise tilted segments in concavity intervals, from which the linear function between the two endpoints in concavity intervals is subtracted.

13. A system according to claim 12, wherein all of the tilted subsegments (N) are evaluated and maximum values ($T_{3tiltmax}$) to ($T_{Ntiltmax}$) on the tilted subsegments in the concavity intervals are determined, where the overall maximum value is the final concave down score (CdS) of the ECG repolarization segment given by equation 2:

$$CdS = \max(\{T_{3tiltmax} \ldots T_{Ntiltmax}\}) \qquad \text{Equation 2.}$$

14. A system according to claim 1, wherein the peakedness of the T wave peak (Peak_Curvature) is evaluated by calculating the radius of curvature value (Rcurv) in Tpeak, which radius of curvature is given by:

$$Rcurv = -\frac{\left[1+\left(\frac{dy}{dx}\right)^2\right]^{3/2}}{\frac{d^2y}{dx^2}}$$

where x is the timescale normalized with the T wave width, and y is the ECG signal normalized with the T wave amplitude.

15. A system according to claim 1, wherein the symmetric properties of the T wave are evaluated by comparing the T wave curve on the right side of Tpeak with the T wave curve on the left side of Tpeak, which comparison of left and right side is performed at any representation of the T wave, such as the time domain ECG signal, the first derivative of the signal, the second derivative of the signal or any combination of these such as the radius of curvature of the signal Rcurv.

16. A system according to claim 15, wherein the Twave representation of the right side of Tpeak is flipped around a vertical line through Tpeak to cover the left side of Tpeak.

17. A system according to claim 16, wherein a first or second derivative is used for the mathematical analysis, where the Twave representation of the right side of Tpeak is flipped around the x axis to compensate for the sign difference between the two sides.

18. A system according to claim 1, wherein the system analyzes ECG curvature for drug influence.

19. A system for analysing ECG curvature according to claim 1, wherein the system analyzes ECG curvature for Long QT Syndrome.

* * * * *